(12) United States Patent
Maggio

(10) Patent No.: US 8,642,564 B2
(45) Date of Patent: Feb. 4, 2014

(54) COMPOSITIONS FOR DRUG ADMINISTRATION

(75) Inventor: Edward T. Maggio, San Diego, CA (US)

(73) Assignee: Aegis Therapeutics, LLC, San Diego, CA (US)

( * ) Notice: Subject to any disclaimer, the term of this patent is extended or adjusted under 35 U.S.C. 154(b) by 1178 days.

(21) Appl. No.: 12/036,963

(22) Filed: Feb. 25, 2008

(65) Prior Publication Data

US 2008/0200418 A1 Aug. 21, 2008

Related U.S. Application Data

(63) Continuation-in-part of application No. 11/193,825, filed on Jul. 29, 2005, which is a continuation-in-part of application No. 11/127,786, filed on May 11, 2005, now abandoned.

(60) Provisional application No. 60/649,958, filed on Feb. 3, 2005, provisional application No. 60/637,284, filed on Dec. 17, 2004, provisional application No. 60/632,038, filed on Nov. 30, 2004, provisional application No. 60/609,890, filed on Sep. 14, 2004, provisional application No. 60/604,296, filed on Aug. 25, 2004.

(51) Int. Cl.
*A61K 31/7028* (2006.01)
*A61K 31/7088* (2006.01)
*C12N 15/113* (2010.01)

(52) U.S. Cl.
USPC ........................... 514/25; 514/44 R; 514/44 A

(58) Field of Classification Search
USPC ......................................... 514/25, 44 R, 44 A
See application file for complete search history.

(56) References Cited

U.S. PATENT DOCUMENTS

| | | | |
|---|---|---|---|
| 3,547,828 | A | 12/1970 | Mansfield et al. |
| 4,397,951 | A | 8/1983 | Taki et al. |
| 4,748,158 | A | 5/1988 | Biermann et al. |
| 5,236,707 | A | 8/1993 | Stewart, II |
| 5,317,010 | A | 5/1994 | Pang et al. |
| 5,369,095 | A | 11/1994 | Kee et al. |
| 5,661,130 | A | 8/1997 | Meezan et al. |
| 5,814,607 | A | 9/1998 | Patton |
| 5,955,425 | A | 9/1999 | Morley et al. |
| 6,316,410 | B1 | 11/2001 | Barbier et al. |
| 6,395,300 | B1 | 5/2002 | Straub et al. |
| 6,495,498 | B2 | 12/2002 | Niemiec et al. |
| 6,524,557 | B1 | 2/2003 | Backstrom et al. |
| 6,794,357 | B1 | 9/2004 | Backstrom et al. ............... 514/2 |
| 6,991,785 | B2 | 1/2006 | Frey, II |
| 7,524,510 | B2* | 4/2009 | Arnold et al. ............ 424/278.1 |
| 2002/0141971 | A1 | 10/2002 | Frey, II |
| 2003/0040497 | A1* | 2/2003 | Teng et al. ..................... 514/44 |
| 2003/0170206 | A1 | 9/2003 | Rasmussen et al. |
| 2004/0147473 | A1 | 7/2004 | Warrel, Jr. |
| 2004/0258663 | A1 | 12/2004 | Quay et al. |
| 2006/0045869 | A1 | 3/2006 | Meezan et al. |
| 2006/0046962 | A1 | 3/2006 | Meezan et al. |
| 2006/0106227 | A1 | 5/2006 | Reddy et al. |
| 2007/0059254 | A1 | 3/2007 | Singh |
| 2007/0098805 | A1 | 5/2007 | Liversidge |
| 2008/0268032 | A1 | 10/2008 | Maggio |
| 2008/0299079 | A1 | 12/2008 | Meezan et al. |
| 2009/0258865 | A1 | 10/2009 | Cartt et al. |
| 2010/0203119 | A1 | 8/2010 | Leane et al. |
| 2010/0209485 | A1 | 8/2010 | Maggio |

FOREIGN PATENT DOCUMENTS

| | | |
|---|---|---|
| EP | 0 396 777 A1 | 11/1990 |
| EP | 1 417 972 A1 | 5/2004 |
| WO | WO 95/00151 A1 | 1/1995 |
| WO | WO 00/01390 A1 | 1/2000 |
| WO | WO 2005/018565 A2 | 3/2005 |

OTHER PUBLICATIONS

Definition of pilus, Merriam-Webster Medical Dictionary, http://www.merriam-webster.com/medical/pilus, accessed online on May 28, 2013.*
Definition of villus, Merriam-Webster Medical Dictionary, http://www.merriam-webster.com/medical/villus, accessed online on May 28, 2013.*
Tillman et al., J. Pharm. Sci., 2008, 97(1), p. 225-236, published online Aug. 22, 2007.*
Definition of prevent, WordNet, http://wordnet.princeton.edu, accessed online Nov. 14, 2007.
"Drug dosage in laboratory animals: A handbook", *Pergamon Press*, Oxford, GB, vol. 4, pp. 138-139, Jan. 1, 1966.
Holford N.H.G. & Benet L.Z., "Pharmacokinetics and Pharmacodynamics: Dose Selection & the Time Course of Drug Action", In: Katzung B.G., ed. *Basic & Clinical Pharmacology* (7th ed.), Appleton & Lange, Stamford, CT, 1998, pp. 34-49.
Fricker et al., "Permeation enhancement of octreotide by specific bile salts in rats and human subjects: in vitro, in vivo correlations", *Br. J. Pharmacol.*, 117(1):217-23 (1996).
Material Safety Data Sheet for Anatrace, Inc., product n-Dodecyl-β-D-maltopyranoside, Anagrade, Dated: Jan. 25, 1994 and Revised: Jul. 15, 2004, http://media.affymetrix.com/support/technical/anatrace/msds/D310.pdf, accessed online on Dec. 13, 2012.
Olesen et al., "The Headaches", *Lippincott Williams & Wilkins*, p. 474 (2005).
Webpage for Anatrace products of Affymetrix, http://www.affymetrix.com/estore/browse/level_three_category_and_products.jsp?category=35843&categoryIdClicked=35843&expand=true&parent=35900, accessed online on Dec. 13, 2012.
European Search Report (ESR) from EP 09 83 5809, dated Nov. 14, 2012.

(Continued)

*Primary Examiner* — Shaojia Anna Jiang
*Assistant Examiner* — Jonathan S Lau
(74) *Attorney, Agent, or Firm* — DLA Piper LLP (US)

(57) ABSTRACT

A composition having at least one alkyl glycoside and at least one therapeutic agent, wherein the alkylglycoside has an alkyl chain length from about 10 to about 16 carbon atoms and wherein the therapeutic agent is an oligonucleotide.

16 Claims, 3 Drawing Sheets

(56) References Cited

OTHER PUBLICATIONS

Ahsan et al., "Effects of the permeability enhancers, tetradecylmaltoside and dimethyl-beta-cyclodextrin, on insulin movement across human bronchial epithelial cells (16HBE14o-)", *Eur. J. Pharm. Sci.*, 20(1):27-34 (2003).

Ahsan et al., "Sucrose cocoate, a component of cosmetic preparations, enhances nasal and ocular peptide absorption", *Int. J. Pharm.*, 251(1-2):195-203 (2003).

Arnold et al., "Correlation of tetradecylmaltoside induced increases in nasal peptide drug delivery with morphological changes in nasal epithelial cells", *J. Pharm. Sci.*, 93(9):2205-2213 (2004).

Chen et al., "Peptide Drug Permeation Enhancement by Select Classes of Lipids", presented at *the 45th American Society of Cell Biology*, S.F., CA, Dec. 10-14, 2005.

Edwards CM., "GLP-1: target for a new class of antidiabetic agents?", *J. R. Soc. Med.*, 97(6):270-274 (2004).

Yu Xinrui et al., "Triptan Medicament and Migraine", *World Pharmacy (Synthetic Drug and Biochemical Drug Formulation Fascicule)*, 22(2):91-92 (2001).

Communication from Chinese Patent Office from application No. CN 200980157305.0, dated Jan. 28, 2013.

Albert et al., "Pharmacokinetics of diphenhydramine in man", *J. Pharmacokinet. Biopharm.*, 3(3):159-170 (1975).

Chavanpatil and Vavia, "Nasal drug delivery of sumatriptan succinate", *Pharmazie.*, May 2005;60(5):347-9.

Chen-Quay et al., "Identification of tight junction modulating lipids", *J. Pharm. Sci.*, 98(2):606-619 (2009).

Davis and Illum, "Absorption enhancers for nasal drug delivery", *Clin. Pharmacokine.*, 2003;42(13)1107-28.

Eley and Triumalashetty, "In vitro assessment of alkylglycosides as permeability enhancers", *AAPS PharmSciTech.*, Oct. 19, 2001;2(3):E19 (pp. 1-7).

Hovgaard et al., "Stabilization of insulin by alkylmaltosides. A. Spectroscopic evaluation", *International Journal of Pharmaceutics*, 132(1-2):107-113 (1996).

Paulsson and Edsman, "Controlled drug release from gels using surfactant aggregates. II. Vesicles formed from mixtures of amphiphilic drugs and oppositely charged surfactants", *Pharm. Res.*, 18(11):1586-1592 (2001).

Shim and Kim, "Administration Route Dependent Bioavailability of Interferon-α and Effect of Bile Salts on the Nasal Absorption", *Drug Development and Industrial Pharmacy*, 19(10):1183-1199 (1993).

Castro et al., "Ecologically safe alkyl glucoside-based gemini surfactants", *ARKIVOC*, xii:253-267 (2005).

De Vry and Schreiber, "Effects of selected serotonin 5-HT(1) and 5-HT(2) receptor agonists on feeding behavior: possible mechanisms of action", *Neurosci. Biobehav. Rev.*, 24(3):341-53 (2000).

Definition downloaded Sep. 13, 2012 at the medical-dictionary. thefreedictionary.com/p/encephalin.

Duquesnoy et al., "Comparative clinical pharmacokinetics of single doses of sumatriptan following subcutaneous, oral, rectal and intranasal administration", *Eur. J. Pharm. Sci.*, 6(2):99-104 (1998).

Lahat et al., "Intranasal midazolam for childhood seizures", *The Lancet*, 352(9128):620 (1998).

Mathew N.T., "Serotonin 1D (5-HT1D) agonists and other agents in acute migraine", *Neurol. Clin.*, 15(1):61-83 (1997).

Phillips A.J., "The challenge of gene therapy and DNA delivery", *J. Pharm. Pharmacol.*, 53(9):1169-1174 (2001).

Pillion et al., "Synthetic long-chain alkyl maltosides and alkyl sucrose esters as enhancers of nasal insulin absorption", *J. Pharm. Sci.*, 91:1456-1462 (2002).

Pirollo and Chang, "Targeted delivery of small interfering RNA: approaching effective cancer therapies", *Cancer Res.*, 68(5):1247-1250 (2008).

Sanders et al., "Pharmacokinetics of ergotamine in healthy volunteers following oral and rectal dosing", *Eur. J. Clin. Pharmacol.*, 30(3):331-334 (1986).

Sigma Online Catalog website: sigmaaldrich.com/catalog/product/sigma/15826?lang=en&region=US, downloaded Aug. 9, 2012; 1 page.

Sigma Online Catalog website: sigmaaldrich.com/catalog/product/sigma/d4641?lang=en&region=US&cm_sp=Customer_Favorites-_-Detail_Page-_-Text-D4641, downloaded Aug. 9, 2012; 1 page.

Turton et al., "A role for glucagon-like peptide-1 in the central regulation of feeding", *Nature*, 379(6560):69-72 (1996).

Vidal et al., "Making sense of antisense", *Eur. J. Cancer*, Dec. 2005;41(18):2812-2818 (2005). Epub. Nov. 9, 2005.

Weber and Benning, "Metabolism of orally administered alkyl beta-glycosides in the mouse", *J. Nutr.*, 114:247-254 (1984).

Definition of drug, Merriam-Webster Dictionary, http://www.merriam-webster.com/dictionary/drug, accessed online on Sep. 8, 2011.

Bhairi S.M., "A guide to the properties and uses of detergents in biological systems", *Calbiochem*, pp. 1-42 (2001).

Hathcox and Beuchat, "Inhibitory effects of sucrose fatty acid esters, alone and in combination with ethylenediaminetetraacetic acid and other organic acids, on viability of *Escherichia coli* 0157:H7", *Food Microbiology*, 13(3):213-225 (1996).

\* cited by examiner

COMPOSITIONS FOR DRUG ADMINISTRATION

CROSS REFERENCE TO RELATED APPLICATION(S)

This application is a continuation-in-part and claims the benefit of priority under 35 U.S.C. §120 of U.S. application Ser. No. 11/193,825, filed Jul. 29, 2005, currently pending, which is a continuation-in-part and claims the benefit of priority under 35 U.S.C. §120 of U.S. application Ser. No. 11/127,786, filed May 11, 2005, currently pending, and claims the benefit of priority under 35 U.S.C. §119(e) of U.S. Application Ser. No. 60/649,958, filed Feb. 3, 2005; the benefit of priority under 35 USC §119(e) of U.S. Application Ser. No. 60/637,284, filed Dec. 17, 2004; the benefit of priority under 35 USC §119(e) of U.S. Application Ser. No. 60/632,038, filed Nov. 30, 2004; the benefit of priority under 35 USC §119(e) of U.S. Application Ser. No. 60/609,890, filed Sep. 14, 2004; and the benefit of priority under 35 USC §119(e) of U.S. Application Ser. No. 60/604,296, filed Aug. 25, 2004. The disclosure of each of the prior applications is considered part of and is incorporated by reference in the disclosure of this application.

BACKGROUND OF THE INVENTION

1. Field of the Invention

The invention relates generally to non-irritating, non-toxic compositions providing enhanced bioavailability and more specifically to alkyl glycoside or saccharide alkyl ester compositions for delivery of therapeutic agents to a subject.

2. Background Information

Therapeutic agents are often combined with various surfactants. Yet, surfactants are frequently irritating to the skin and other tissues, including mucosal membranes such as those found in the nose, mouth, eye, vagina, rectum, esophagus, intestinal tract, and the like. Many surfactants also cause proteins to denature, thus destroying their biological activity. Another serious limitation to the development and use of such agents is the ability to deliver them safely, non-invasively, efficiently and stably to the site of action. Therefore, an ideal enhancing surfactant will stabilize the therapeutic agent, be non-toxic and non-irritable to the skin or mucosal surfaces, have antibacterial activity, and enhance the passage or absorption of the therapeutic agent through various membrane barriers without damaging the structural integrity and biological function of the membrane and increase bioavailability of the agent.

SUMMARY OF THE INVENTION

The present invention is based, in part, on the development of a therapeutic composition containing a drug enhancing agent useful for increasing the absorption and bioavailability of the drug, while at the same time avoiding various adverse toxic effects of drug. In particular, the drug enhancing agents of the invention contain a non-toxic surfactant consisting of at least an alkyl glycoside and/or saccharide alkyl ester. One advantage of the therapeutic compositions of the invention is that they permit administration and delivery of the therapeutic agents with high bioavailabilities at concentrations of enhancing agents that are dramatically below their so-called "no observable adverse effect levels" (their NOAEL's). Accordingly, the present invention provides compositions, including alkyl glycosides and/or saccharide alkyl esters and a therapeutic agent (e.g. small molecule organic drug molecules, low molecular weight peptides such as Exenatide, GLP-1 and the like, proteins, and non-peptide therapeutic polymers such as low molecular weight heparin and inhibitory RNA), methods of administering and using the compositions e.g. via the oral, ocular, nasal, nasolacrimal, inhalation or pulmonary, oral cavity (sublingual or Buccal cell) or cerebral spinal fluid (CSF) delivery route, and methods of ameliorating a disease state in a subject by administration of such compositions In one aspect, the present invention relates to a surfactant composition having at least one alkyl glycoside and/or at least one saccharide alkyl ester, and when admixed, mixed or blended with a therapeutic agent, a drug, or biologically active compound, the surfactant stabilizes the biological activity and increases the bioavailability of the drug.

Accordingly, in one aspect, the invention provides a therapeutic composition having at least one biologically active compound and at least one surfactant, wherein the surfactant further consists of at least one alkyl glycoside and/or saccharide alkyl ester or sucrose ester and wherein the therapeutic composition stabilizes the biologically active compound for at least about 6 months, or more, and from about 4° C. to about 25° C.

The invention also provides a method of administering a therapeutic composition having a surfactant including at least one alkyl glycoside and/or saccharide alkyl ester admixed, mixed, or blended with at least one therapeutic agent, or a drug, or biologically active compound, and administered or delivered to a subject, wherein the alkyl has from about 10 to 24, 10 to 20, 10 to 16, or 10 to 14 carbon atoms, wherein the surfactant increases the stability and bioavailability of the therapeutic agent.

In yet another aspect, the invention provides a method of increasing absorption of a low molecular weight compound into the circulatory system of a subject by administering the compound via the oral, ocular, nasal, nasolacrimal, inhalation or pulmonary, oral cavity (sublingual or Buccal cell), or CSF delivery route when admixed, mixed or blended with an absorption increasing amount of a suitable surfactant, wherein the surfactant is a nontoxic and nonionic hydrophobic alkyl joined by a linkage to a hydrophilic saccharide. Such low molecular weight compounds include but are not limited to, nicotine, interferon, PYY, GLP-1, synthetic exendin-4, parathyroid hormone, human growth hormone, or a small organic molecule. Additional low molecular weight compounds include antisense oligonucleotides or interfering RNA molecules (e.g., siRNA or RNAi).

The present invention also provides a method of treating diabetes including administering to a subject in need thereof via the oral, ocular, nasal, nasolacrimal, inhalation or pulmonary, or oral cavity (sublingual or Buccal cell), a blood glucose reducing amount of a therapeutic composition, for example, an incretin mimetic agent or a functional equivalent thereof, and an absorption increasing amount of a suitable nontoxic, nonionic alkyl glycoside having a hydrophobic alkyl group joined by a linkage to a hydrophilic saccharide, thereby increasing the absorption of incretin mimetic agent or insulin and lowering the level of blood glucose and treating diabetes in the subject.

The present invention also provides a method of treating congestive heart failure in a subject including administering to the subject in need thereof via the oral, ocular, nasal, nasolacrimal, or inhalation delivery route, a therapeutically effective amount of a composition comprising a GLP-1 peptide or a functional equivalent thereof, and an absorption increasing amount of a suitable nontoxic, nonionic alkyl glycoside having a hydrophobic alkyl joined by a linkage to a hydrophilic saccharide, thereby treating the subject.

In another aspect, the invention provides a method of treating obesity or diabetes associated with obesity in a subject comprising administering to a subject in need thereof via the oral, ocular, nasal, nasolacrimal, inhalation or CSF delivery route, a therapeutically effective amount of a composition comprising a PYY peptide or a functional equivalent thereof, and an absorption increasing amount of a suitable nontoxic, nonionic alkyl glycoside having a hydrophobic alkyl joined by a linkage to a hydrophilic saccharide, thereby treating the subject.

In another aspect, the invention provides a method of increasing absorption of a low molecular weight therapeutic compound into the circulatory system of a subject by administering via the oral, ocular, nasal, nasolacrimal, inhalation or CSF delivery route the compound and an absorption increasing amount of a suitable nontoxic, nonionic alkyl glycoside having a hydrophobic alkyl group joined by a linkage to a hydrophilic saccharide, wherein the compound is from about 1-30 kD, with the proviso that the compound is not insulin, calcitonin, or glucagon when the route of administration is oral, ocular, nasal, or nasolacrimal.

The present invention also provides a method of increasing absorption of a low molecular weight therapeutic compound into the circulatory system of a subject by administering via the oral, ocular, nasal, nasolacrimal, inhalation or pulmonary, oral cavity (sublingual or Buccal cell) or CSF delivery route the compound and an absorption increasing amount of a suitable nontoxic, nonionic alkyl glycoside having a hydrophobic alkyl joined by a linkage to a hydrophilic saccharide, wherein the compound is from about 1-30 kilo Daltons (kD), with the proviso that the subject does not have diabetes when delivery is via the oral, ocular, nasal or nasolacrimal routes.

In one aspect of the invention, there is provided a pharmaceutical composition having a suitable nontoxic, nonionic alkyl glycoside having a hydrophobic alkyl group joined by a linkage to a hydrophilic saccharide in combination with a therapeutically effective amount of Exenatide (exendin-4) in a pharmaceutically acceptable carrier.

In one aspect, the invention provides a pharmaceutical composition having a suitable nontoxic, nonionic alkyl glycoside having a hydrophobic alkyl group joined by a linkage to a hydrophilic saccharide in combination with a therapeutically effective amount of GLP-1 in a pharmaceutically acceptable carrier.

In one aspect, the invention provides a pharmaceutical composition having a suitable nontoxic, nonionic alkyl glycoside having a hydrophobic alkyl group joined by a linkage to a hydrophilic saccharide in combination with a therapeutically effective amount of nicotine in a pharmaceutically acceptable carrier.

In one aspect, the invention provides a pharmaceutical composition comprising a suitable nontoxic, nonionic alkyl glycoside having a hydrophobic alkyl group joined by a linkage to a hydrophilic saccharide in combination with a therapeutically effective amount of interferon in a pharmaceutically acceptable carrier.

In one aspect, the invention provides pharmaceutical composition having a suitable nontoxic, nonionic alkyl glycoside having a hydrophobic alkyl group joined by a linkage to a hydrophilic saccharide in combination with a therapeutically effective amount of PYY in a pharmaceutically acceptable carrier.

In one aspect, the invention provides a pharmaceutical composition having a suitable nontoxic, nonionic alkyl glycoside having a hydrophobic alkyl group joined by a linkage to a hydrophilic saccharide in combination with a therapeutically effective amount of parathyroid hormone in a pharmaceutically acceptable carrier.

In one aspect, the invention provides a pharmaceutical composition having a suitable nontoxic, nonionic alkyl glycoside having a hydrophobic alkyl group joined by a linkage to a hydrophilic saccharide in combination with a therapeutically effective amount of a peptide having a molecular weight of about 1-75 kD in a pharmaceutically acceptable carrier, with the proviso that the peptide is not insulin, calcitonin, and glucagon.

In one aspect, the invention provides a pharmaceutical composition having a suitable nontoxic, nonionic alkyl glycoside having a hydrophobic alkyl group joined by a linkage to a hydrophilic saccharide in combination with a therapeutically effective amount erythropoietin in a pharmaceutically acceptable carrier.

In one aspect, the invention provides a pharmaceutical composition having a therapeutically effective amount of an oligonucleotide in combination with an absorption increasing amount of an alkylglycoside. The oligonucleotide can be an antisense oligonucleotide or interfering RNA molecules, such as siRNA or RNAi. The oligonucleotide typically has a molecular weight of about 1-20 kD and is from about 1-100, 1-50, 1-30, 1-25 or 15-25 nucleotides in length. In another aspect, the oligonucleotide has a molecular weight of about 5-10 kD. In one aspect, the alkylglycoside is tetradecyl-beta-D-maltoside.

In yet another aspect, the invention provides a method of increasing the bioavailability of a low molecular weight oligonucleotide in a subject by administering the compound with an absorption increasing amount of an alkylglycoside, thereby increasing the bioavailability of the compound in the subject. In one aspect, the alkylglycoside is tetradecyl-beta-D-maltoside.

In one aspect, the invention provides a method of increasing absorption of a compound into the CSF of a subject having administered intranasally the compound and an absorption increasing amount of a suitable nontoxic, nonionic alkyl glycoside having a hydrophobic alkyl group joined by a linkage to a hydrophilic saccharide.

In yet another aspect, the invention provides a pharmaceutical composition having a suitable nontoxic, nonionic alkyl glycoside having a hydrophobic alkyl group joined by a linkage to a hydrophilic saccharide in combination with a mucosal delivery-enhancing agent selected from:
    (a) an aggregation inhibitory agent;
    (b) a charge-modifying agent;
    (c) a pH control agent;
    (d) a degradative enzyme inhibitory agent;
    (e) a mucolytic or mucus clearing agent;
    (f) a ciliostatic agent;
    (g) a membrane penetration-enhancing agent selected from:
        (i) a surfactant; (ii) a bile salt; (ii) a phospholipid additive, mixed micelle, liposome, or carrier; (iii) an alcohol; (iv) an enamine; (v) an NO donor compound; (vi) a long-chain amphipathic molecule; (vii) a small hydrophobic penetration enhancer; (viii) sodium or a salicylic acid derivative; (ix) a glycerol ester of acetoacetic acid; (x) a cyclodextrin or beta-cyclodextrin derivative; (xi) a medium-chain fatty acid; (xii) a chelating agent; (xiii) an amino acid or salt thereof; (xiv) an N-acetylamino acid or salt thereof; (xv) an enzyme degradative to a selected membrane component; (ix) an inhibitor of fatty acid synthesis; (x) an inhibitor of cholesterol synthesis; and (xi) any combination of the membrane penetration enhancing agents recited in (i)-(x);
(h) a modulatory agent of epithelial junction physiology;
(i) a vasodilator agent;
(j) a selective transport-enhancing agent; and
(k) a stabilizing delivery vehicle, carrier, mucoadhesive, support or complex-forming species with which the compound is effectively combined, associated, contained, encapsulated or bound resulting in stabilization of the compound for enhanced nasal mucosal delivery, wherein the formulation of the compound with the intranasal delivery-enhancing agents provides for increased bioavailability of the compound in a blood plasma of a subject.

In one aspect, the invention provides a method of increasing absorption of a low molecular weight compound into the circulatory system of a subject by administering, via the oral, ocular, nasal, nasolacrimal, inhalation or pulmonary, oral cavity (sublingual or Buccal cell) or CSF delivery route (a) the compound; (b) an absorption increasing amount of a suitable nontoxic, nonionic alkyl glycoside having a hydrophobic alkyl group joined by a linkage to a hydrophilic saccharide; and (c) a mucosal delivery-enhancing agent.

In one aspect, the invention provides a method of controlling caloric intake by administering a composition having a therapeutic effective amount of exendin-4, or related GLP-1 peptide, with an effective amount of Intravail alkyl saccharide.

In another aspect, the invention provides a method of controlling blood glucose levels in a subject by administering to a subject a composition comprising a therapeutic effective amount of exendin-4, or related GLP-1 peptide, with an effective amount of Intravail alkyl saccharide.

Still, in another aspect, the invention provides a controlled release dosage composition comprising:
(a) a core comprising:
  (i) at least one therapeutic agent or drug;
  (ii) at least one alkyl glycoside and/or saccharide alkyl ester; and
(b) at least one membrane coating surrounding the core, wherein the coating is impermeable, permeable, semi-permeable or porous and becomes more permeable upon sustained contact with contents of the gastrointestinal tract.

In another embodiment, the invention provides a method of administering an alkylglycoside composition by administering a therapeutically effective amount of at least one alkylglycoside having an alkyl chain length from about 12 to about 14 carbon atoms, at least one saccharide with an antibacterial activity, and at least one therapeutic agent.

Still in another embodiment, the invention provides a composition having at least one drug selected from the group consisting of insulin, PYY, Exendin-4 or other GLP-1 related peptide, human growth hormone, calcitonin, parathyroid hormone, truncated parathyroid hormone peptides such as PTH 1-34, EPO, interferon alpha, interferon beta, interferon gamma, and GCSF and at least one alkyl saccharide having antibacterial activity.

In one aspect, the invention provides an antibacterial alkyl saccharide composition, which includes n-Dodecyl-4-O-α-D-glucopyranosyl-β-D-glucopyranoside or n-tetradecyl-4-O-α-D-glucopyranosyl-β-D-glucopyranoside.

Yet, in another aspect, the invention provides an aqueous drug composition for transmucocal or transdermal administration having at least one drug and at least one antibacterial agent in a concentration from about 0.05% to about 0.5%.

DETAILED DESCRIPTION OF THE INVENTION

Figure 1:
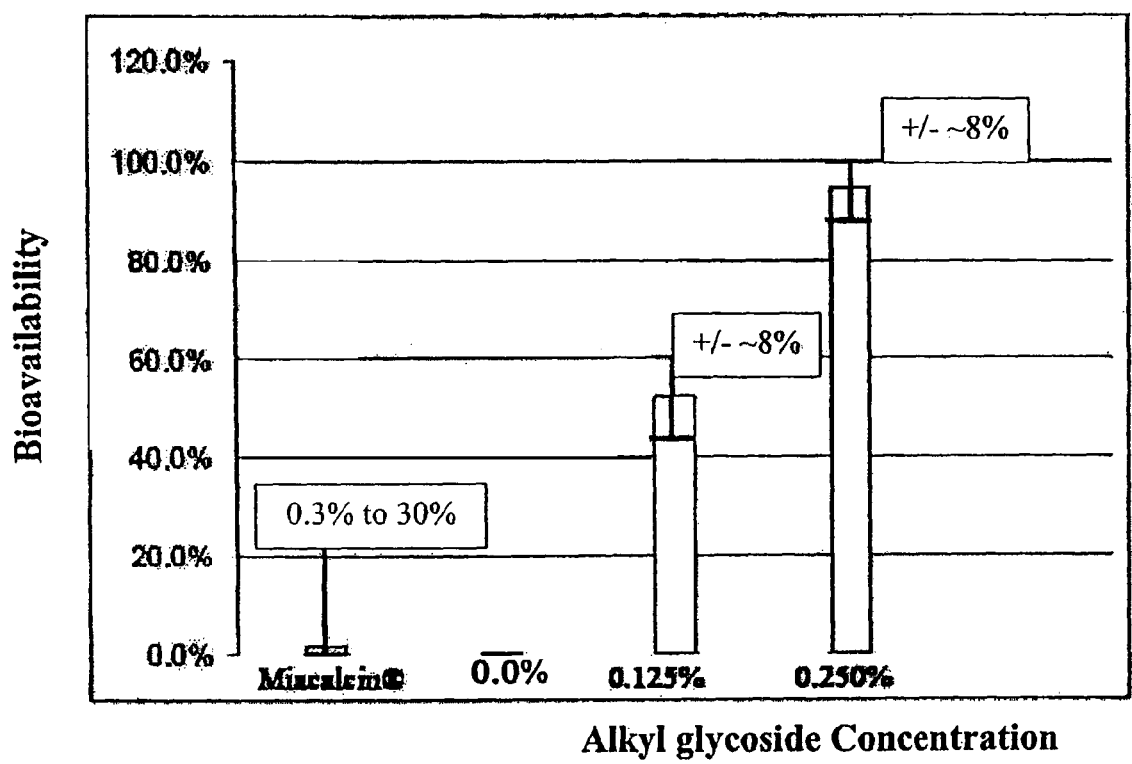
FIG. 1 is a graph showing the intranasal percent bioavailability compared to intravenous injection and the subject-to-subject coefficients of variation for MIACALCIN® (salmon calcitonin) with and without alkyl glycoside.

The present invention may be understood more readily by reference to the following detailed description of specific embodiments and the Examples included therein.

The present invention is based on the discovery that therapeutic compositions comprising of least one drug and at least one surfactant, wherein the surfactant is comprised of at least one alkyl glycoside and/or at least one saccharide alkyl ester are stable, non-toxic, non-irritating, anti-bacterial compositions that increase bioavailability of the drug and have no observable adverse effects when administered to a subject.

A "therapeutic composition" can consist of an admixture with an organic or inorganic carrier or excipient, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary stabilizing, thickening or coloring agents can be used, for example a stabilizing dry agent such as triulose.

A "drug" is any therapeutic compound, or molecule, or therapeutic agent, or biologically active compound, including but not limited to nucleic acids, small molecules, proteins, polypeptides or peptides and the like.

The term "nucleic acids" or "oligonucleotide" also denotes DNA, cDNA, RNA, siRNA, RNAi, dsRNA and the like, which encode translated and untranslated regions or inhibits translated or untranslated regions of structural genes encoding a peptide or protein or regulatory region. For example, a nucleic acid of the invention can include 5' and 3' untranslated regulatory nucleotide sequences as well as translated sequences associated with a structural gene. The term "nucleic acids" or "oligonucleotide" or grammatical equivalents as used herein, refers to at least two nucleotides covalently linked together.

Additionally, the term "oligonucleotide" refers to structures including modified portions such as modified sugar moieties, modified base moieties or modified sugar linking moieties. These modified portions function in a manner similar to natural bases, natural sugars and natural phosphodiester linkages. Accordingly, oligonucleotides may have altered base moieties, altered sugar moieties or altered inter-sugar linkages. Modified linkages may be, for example, phosphoramide, phosphorothioate, phosphorodithioate, methyl phosphonate, phosphotriester, phosphoramidate, O-methylphosphoroamidite linkages, or peptide nucleic acid backbones and linkages. Other analogs may include oligonucleotides with positive backbones, non-ionic backbones and non-ribose backbones. The nucleic acid may be DNA, both genomic and cDNA, RNA or a hybrid, where the nucleic acid contains any combination of deoxyribo- and ribo-nucleotides, and any combination of natural or modified bases, including uracil, adenine, thymine, cytosine, guanine, inosine, xathanine, hypoxathanine, isocytosine, isoguanine, halogentated bases and the like. Other modifications may include, for example, deaza or aza purines and pyrimidines used in place of natural purine and pyrimidine bases; pyrimidine bases having substituent groups at the 5- or 6-positions, purine bases having altered or replacement substituent groups at the 2-, 6- or 8-positions, or sugars having substituent groups at their 2'-position, substitutions for one or more of the hydrogen atoms of the sugar, or carbocyclic or acyclic sugars.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation.

Antisense molecules include oligonucleotides comprising a singe-stranded nucleic acid sequence (either RNA or DNA) capable of binding to target receptor or ligand mRNA (sense) or DNA (antisense) sequences. The ability to derive an antisense or a sense oligonucleotide, based upon a cDNA sequence encoding a given protein. Antisense or sense oligonucleotides further comprise oligonucleotides having modified sugar-phosphodiester backbones and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

RNAi is a phenomenon in which the introduction of dsRNA into a diverse range of organisms and cell types causes degradation of the complementary mRNA. In the cell, long dsRNAs are cleaved into short (e.g., 21-25 nucleotide) small interfering RNAs (siRNAs), by a ribonuclease. The siRNAs subsequently assemble with protein components into an RNA-induced silencing complex (RISC), unwinding in the process. The activated RISC then binds to complementary transcripts by base pairing interactions between the siRNA antisense strand and the mRNA. The bound mRNA is then cleaved and sequence specific degradation of mRNA results in gene silencing. As used herein, "silencing" refers to a mechanism by which cells shut down large sections of chromosomal DNA resulting in suppressing the expression of a particular gene. The RNAi machinery appears to have evolved to protect the genome from endogenous transposable elements and from viral infections. Thus, RNAi can be induced by introducing nucleic acid molecules complementary to the target mRNA to be degraded.

Other examples of sense or antisense oligonucleotides include those oligonucleotides which are covalently linked to organic moieties and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

A peptide of the invention may be any medically or diagnostically useful peptide or protein of small to medium size (i.e. up to about 15 kD, 30 kD, 40 kD, 50 kD, 60 kD, 70 kD, 80 kD, 90 kD, 100 kD, for example). The mechanisms of improved polypeptide absorption are described in U.S. Pat. No. 5,661,130 which is hereby incorporated by reference in its entirety. Invention compositions can be mixed with all such peptides, although the degree to which the peptide benefits are improved may vary according to the molecular weight and the physical and chemical properties of the peptide, and the particular surfactant used. Examples of polypeptides include vasopressin, vasopressin polypeptide analogs, desmopressin, glucagon, corticotropin (ACTH), gonadotropin, calcitonin, C-peptide of insulin, parathyroid hormone (PTH), growth hormone (HG), human growth hormone (hGH), growth hormone releasing hormone (GHRH), oxytocin, corticotropin releasing hormone (CRH), somatostatin or somatostatin polypeptide analogs, gonadotropin agonist or gonadotrophin agonist polypeptide analogs, human atrial natriuretic peptide (ANP), human thyroxine releasing hormone (TRH), follicle stimulating hormone (FSH), prolactin, insulin, insulin like growth factor-I (IGF-I) somatomedin-C (SM-C), calcitonin, leptin and the leptin derived short peptide OB-3, melatonin, GLP-1 or Glucagon-like peptide-1, GiP, neuropeptide pituitary adenylate cyclase, GM-1 ganglioside, nerve growth factor (NGF), nafarelin, D-tryp6)-LHRH, FGF, VEGF antagonists, leuprolide, interferon (e.g., $\alpha$, $\beta$, $\gamma$) low molecular weight heparin, PYY, LHRH antagonists, Keratinocyte Growth Factor (KGF), Glial-Derived Neurotrophic Factor (GDNF), ghrelin, and ghrelin antagonists. Further, in some aspects, the peptide or protein is selected from a growth factor, interleukin, polypeptide vaccine, enzyme, endorphin, glycoprotein, lipoprotein, or a polypeptide involved in the blood coagulation cascade.

Other drugs or therapeutic compounds, molecules and/or agents include compounds or molecules of the central nervous system affecting neurotransmitters or neural ion channels (i.e. antidepressants (bupropion)), selective serotonin 2c receptor agonists, anti-seizure agents (topiramate, zonisamide), some dopamine antagonists, and cannabinoid-1 receptor antagonists (rimonabant)); leptin/insulin/central nervous system pathway agents (i.e. leptin analogues, leptin transport and/or leptin receptor promoters, ciliary neurotrophic factor (Axokine), neuropeptide Y and agouti-related peptide antagonists, proopiomelanocortin, cocaine and amphetamine regulated transcript promoters, alpha-melanocyte-stimulating hormone analogues, melanocortin-4 receptor agonists, protein-tyrosine phosphatase-1B inhibitors, peroxisome proliferator activated receptor-gamma receptor antagonists, short-acting bromocriptine (ergoset), somatostatin agonists (octreotide), and adiponectin); gastrointestinal-neural pathway agents (i.e. agents that increase glucagon-like peptide-1 activity (extendin-4, liraglutide, dipeptidyl peptidase IV inhibitors), protein YY3-36, ghrelin, ghrelin antagonists, amylin analogues (pramlintide)); and compounds or molecules that may increase resting metabolic rate "selective" beta-3 stimulators/agonist, melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type 1 activity, corticotropin-releasing hormone agonists, inhibitors of fatty acid synthesis, carboxypeptidase inhibitors, and gastrointestinal lipase inhibitors (ATL962).

The therapeutic composition of the invention includes a drug and a drug absorption enhancing agent, for example, a surfactant. The term "surfactant" is any surface active agent that modifies interfacial tension of water. Typically, surfactants have one lipophilic and one hydrophilic group in the molecule. Broadly, the group includes soaps, detergents, emulsifiers, dispersing and wetting agents, and several groups of antiseptics. More specifically, surfactants include stearyltriethanolamine, sodium lauryl sulfate, laurylaminopropionic acid, lecithin, benzalkonium chloride, benzethonium chloride and glycerin monostearate; and hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose.

Preferably, the surfactant of the invention consists of at least one suitable alkyl glycoside. As used herein, "alkyl glycoside" refers to any sugar joined by a linkage to any hydrophobic alkyl, as is known in the art. Any "suitable" alkyl glycoside means one that fulfills the limiting characteristics of the invention, i.e., that the alkyl glycoside be nontoxic and nonionic, and that it increases the absorption of a compound when it is administered with the compound via the ocular, nasal, nasolacrimal, inhalation or pulmonary, oral cavity (sublingual or Buccal cell), or CSF delivery route. Suitable compounds can be determined using the methods set forth herein.

Alkyl glycosides of the invention can be synthesized by known procedures, i.e., chemically, as described, e.g., in Rosevear et al., *Biochemistry* 19:4108-4115 (1980) or Koeltzow and Urfer, *J. Am. Oil Chem. Soc.*, 61:1651-1655 (1984), U.S. Pat. No. 3,219,656 and U.S. Pat. No. 3,839,318 or enzymatically, as described, e.g., in Li et al., *J. Biol. Chem.*, 266:10723-10726 (1991) or Gopalan et al., *J. Biol. Chem.* 267:9629-9638 (1992).

Alkyl glycosides of the present invention can include, but are not limited to: alkyl glycosides, such as octyl-, nonyl-, decyl-, undecyl-, dodecyl-, tridecyl-, tetradecyl-, pentadecyl-, hexadecyl-, heptadecyl-, and octadecyl-α- or β-D-maltoside, -glucoside or -sucroside (synthesized according to Koeltzow and Urfer; Anatrace Inc., Maumee, Ohio; Calbiochem, San Diego, Calif.; Fluka Chemie, Switzerland); alkyl thiomaltosides, such as heptyl, octyl, dodecyl-, tridecyl-, and tetradecyl-β-D-thiomaltoside (synthesized according to Defaye, J. and Pederson, C., "Hydrogen Fluoride, Solvent and Reagent for Carbohydrate Conversion Technology" in Carbohydrates as Organic Raw Materials, 247-265 (F. W. Lichtenthaler, ed.) VCH Publishers, New York (1991); Ferenci, T., J. Bacteriol, 144:7-11 (1980)); alkyl thioglucosides, such as heptyl- or octyl 1-thio α- or β-D-glucopyranoside (Anatrace, Inc., Maumee, Ohio; see Saito, S. and Tsuchiya, T. Chem. Pharm. Bull. 33:503-508 (1985)); alkyl thiosucroses (synthesized according to, for example, Binder, T. P. and Robyt, J. F., Carbohydr. Res. 140:9-20 (1985)); alkyl maltotriosides (synthesized according to Koeltzow and Urfer); long chain aliphatic carbonic acid amides of sucrose β-amino-alkyl ethers; (synthesized according to Austrian Patent 382,381 (1987); Chem. Abstr., 108:114719 (1988) and Gruber and Greber pp. 95-116); derivatives of palatinose and isomaltamine linked by amide linkage to an alkyl chain (synthesized according to Kunz, M., "Sucrose-based Hydrophilic Building Blocks as Intermediates for the Synthesis of Surfactants and Polymers" in Carbohydrates as Organic Raw Materials, 127-153); derivatives of isomaltamine linked by urea to an alkyl chain (synthesized according to Kunz); long chain aliphatic carbonic acid ureides of sucrose β-amino-alkyl ethers (synthesized according to Gruber and Greber, pp. 95-116); and long chain aliphatic carbonic acid amides of sucrose β-amino-alkyl ethers (synthesized according to Austrian Patent 382, 381 (1987), Chem. Abstr., 108:114719 (1988) and Gruber and Greber, pp. 95-116).

Surfactants of the invention consisting of an alkyl glycoside and/or a sucrose ester have characteristic hydrophile-lipophile balance (HLB) numbers, which can be calculated or determined empirically (Schick, M. J. Nonionic Surfactants, p. 607 (New York: Marcel Dekker, Inc. (1967)). The HLB number is a direct reflection of the hydrophilic character of the surfactant, i.e., the larger the HLB number, the more hydrophilic the compound. HLB numbers can be calculated by the formula: (20 times MW hydrophilic component)/(MW hydrophobic component+MW hydrophilic component), where MW=molecular weight (Rosen, M. J., Surfactants and Interfacial Phenomena, pp. 242-245, John Wiley, New York (1978)). The HLB number is a direct expression of the hydrophilic character of the surfactant, i.e., the larger the HLB number, the more hydrophilic the compound. A preferred surfactant has an HLB number of from about 10 to 20 and an even more preferred range of from about 11 to 15.

As described above, the hydrophobic alkyl can thus be chosen of any desired size, depending on the hydrophobicity desired and the hydrophilicity of the saccharide moiety. For example, one preferred range of alkyl chains is from about 9 to about 24 carbon atoms. An even more preferred range is from about 9 to about 16 or about 14 carbon atoms. Similarly, some preferred glycosides include maltose, sucrose, and glucose linked by glycosidic linkage to an alkyl chain of 9, 10, 12, 13, 14, 16, 18, 20, 22, or 24 carbon atoms, e.g., nonyl-, decyl-, dodecyl- and tetradecyl sucroside, glucoside, and maltoside, etc. These compositions are nontoxic, since they are degraded to an alcohol and an oligosaccharide, and amphipathic.

The surfactants of the invention can also include a saccharide. As use herein, a "saccharide" is inclusive of monosaccharides, oligosaccharides or polysaccharides in straight chain or ring forms, or a combination thereof to form a saccharide chain. Oligosaccharides are saccharides having two or more monosaccharide residues. The saccharide can be chosen, for example, from any currently commercially available saccharide species or can be synthesized. Some examples of the many possible saccharides to use include glucose, maltose, maltotriose, maltotetraose, sucrose and trehalose. Preferable saccharides include maltose, sucrose and glucose.

The surfactants of the invention can likewise consist of a sucrose ester. As used herein, "sucrose esters" are sucrose esters of fatty acids and is a complex of sucrose and fatty acid. Sucrose esters can take many forms because of the eight hydroxyl groups in sucrose available for reaction and the many fatty acid groups, from acetate on up to larger, more bulky fatty acids that can be reacted with sucrose. This flexibility means that many products and functionalities can be tailored, based on the fatty acid moiety used. Sucrose esters have food and non-food uses, especially as surfactants and emulsifiers, with growing applications in pharmaceuticals, cosmetics, detergents and food additives. They are biodegradable, non-toxic and mild to the skin.

The surfactants of the invention have a hydrophobic alkyl group linked to a hydrophilic saccharide. The linkage between the hydrophobic alkyl group and the hydrophilic saccharide can include, among other possibilities, a glycosidic, thioglycosidic (Horton), amide (Carbohydrates as Organic Raw Materials, F. W. Lichtenthaler ed., VCH Publishers, New York, 1991), ureide (Austrian Pat. 386,414 (1988); Chem. Abstr. 110:137536p (1989); see Gruber, H. and Greber, G., "Reactive Sucrose Derivatives" in Carbohydrates as Organic Raw Materials, pp. 95-116) or ester linkage (Sugar Esters: Preparation and Application, J. C. Colbert ed., (Noyes Data Corp., New Jersey), (1974)). Further, preferred glycosides can include maltose, sucrose, and glucose linked by glycosidic linkage to an alkyl chain of about 9-16 carbon atoms, e.g., nonyl-, decyl-, dodecyl- and tetradecyl sucroside, glucoside, and maltoside. Again, these compositions are amphipathic and nontoxic, because they degrade to an alcohol and an oligosaccharide.

The above examples are illustrative of the types of glycosides to be used in the methods claimed herein, but the list is not exhaustive. Derivatives of the above compounds which fit the criteria of the claims should also be considered when choosing a glycoside. All of the compounds can be screened for efficacy following the methods taught herein and in the examples.

The compositions of the present invention can be administered in a format selected from the group consisting of a tablet, a capsule, a suppository, a drop, a spray, an aerosol and a sustained release or delayed burst format. The spray and the aerosol can be achieved through use of an appropriate dispenser. The sustained release format can be an ocular insert, erodible microparticulates, swelling mucoadhesive particulates, pH sensitive microparticulates, nanoparticles/latex systems, ion-exchange resins and other polymeric gels and implants (Ocusert, Alza Corp., California; Joshi, A., S. Ping and K. J. Himmelstein, Patent Application WO 91/19481). These systems maintain prolonged drug contact with the absorptive surface preventing washout and nonproductive drug loss. The prolonged drug contact is non-toxic to the skin and mucosal surfaces.

The surfactant compositions of the invention are stable. For example, Baudys et al. in U.S. Pat. No. 5,726,154 show that calcitonin in an aqueous liquid composition comprising SDS (sodium dodecyl sulfate, a surfactant) and an organic acid is stable for at least 6 months. Similarly, the surfactant compositions of the present invention have improved stabilizing characteristics when admixed with a drug. No organic acid is required in these formulations. For example, the composition of the invention maintains the stability of proteins and peptide therapeutics for about 6 months, or more, when maintained at about 4° C. to 25° C.

The stability of the surfactant compositions are, in part, due to their high no observable adverse effect level (NOAEL). The Environmental Protection Agency (EPA) defines the no observable adverse effect level (NOAEL) as the exposure level at which there are no statistically or biologically significant increases in the frequency or severity of adverse effects between the exposed population and its appropriate control. Hence, the term, "no observable adverse effect level" (or NOAEL) is the greatest concentration or amount of a substance, found by experiment or observation, which causes no detectable adverse alteration of morphology, functional capacity, growth, development, or life span of the target organism under defined conditions.

The Food and Agriculture Organization (FAO) of the United Nations of the World Health Organization (WHO) has shown that some alkyl glycosides have very high NOAELs, allowing for increased consumption of these alkyl glycosides without any adverse effect. This report can be found on the world wide web at inchem.org/documents/jecfa/jecmono/v10je11.htm. For example, the NOAEL for sucrose dodecanoate, a sucrose ester used in food products, is about 20-30 grams/kilogram/day, e.g. a 70 kilogram person (about 154 lbs.) can consume about 1400-2100 grams (or about 3 to 4.6 pounds) of sucrose dodecanoate per day without any observable adverse effect. Typically, an acceptable daily intake for humans is about 1% of the NOAEL, which translates to about 14-21 grams, or 14 million micrograms to 21 million micrograms, per day, indefinitely. Definitions of NOAELs and other related definitions can be found on the world wide web at epa.gov/OCEPAterms. Thus, although some effects may be produced with alkyl glycoside levels anticipated in the present invention, the levels are not considered adverse, or precursors to adverse effects.

Accordingly, a subject treated with surfactant compositions of the invention having at least one alkyl glycoside, e.g. tetradecylmaltoside (TDM; or Intravail A), at a concentration of about 0.125% by weight of alkyl glycoside two times per day, or three times per day, or more depending on the treatment regimen consumes about 200 to 300 micrograms per day total of TDM. So, the effective dose of the TDM is at least 1000× fold lower than (i.e., $\frac{1}{1000}$) of the NOAEL, and falls far below 1% of the NOAEL, which is the acceptable daily intake; or in this case about $\frac{1}{50,000}$ of the acceptable daily intake. Stated another way, alkyl glycosides of the present invention have a high NOAEL, such that the amount or concentration of alkyl glycosides used in the present invention do not cause an adverse effect and can be safely consumed without any adverse effect.

The surfactant compositions of the invention are also stable because they are physiologically non-toxic and non-irritants. The term, "nontoxic" means that the alkyl glycoside molecule has a sufficiently low toxicity to be suitable for human administration and consumption. Preferred alkyl glycosides are non-irritating to the tissues to which they are applied. Any alkyl glycoside used should be of minimal or no toxicity to the cell, such that it does not cause damage to the cell. Yet, toxicity for any given alkyl glycoside may vary with the concentration of alkyl glycoside used. It is also beneficial if the alkyl glycoside chosen is metabolized or eliminated by the body and if this metabolism or elimination is done in a manner that will not be harmfully toxic. The term, "non-irritant" means that the agent does not cause inflammation following immediate, prolonged or repeated contact with the skin surface or mucous membranes.

Moreover, one embodiment of the surfactant compositions, in particular, the sucrose esters, serve as anti-bacterial agents. An agent is an "anti-bacterial" agent or substance if the agent or its equivalent destroy bacteria, or suppress bacterial growth or reproduction. The anti-bacterial activity of sucrose esters and their fatty acids have been reported. Tetsuaki et al. (1997) "Lysis of *Bacillus subtilis* cells by glycerol and sucrose esters of fatty acids," *Applied and Environmental Microbiology*, 53(3):505-508. Watanabe et al. (2000) describe that galactose and fructose laureates are particularly effective carbohydrate monoesters. Watanabe et al., (2000) "Antibacterial carbohydrate monoesters suppressing cell growth of *Streptococcus mutan* in the presence of sucrose," *Curr Microbiol* 41(3): 210-213. Hence, the present invention is not limited to the sucrose ester described herein, but encompasses other carbohydrate esters, including galactose and fructose esters, that suppress bacterial growth and reproduction.

In general, all useful antimicrobial agents are toxic substances. See Sutton and Porter (2002), "Development of the antimicrobial effectiveness test as USP Chapter <51>," 56(6): 300-311, which is incorporated herein by reference in its entirety. For example, commonly used antimicrobial agents such as benzalkonium chloride are highly toxic as demonstrated by electron micrograph studies in which significant disruption of the mucociliary surfaces are observed at concentrations of benzalkonium far below what is commonly used in intranasal formulations. See for example Sebahattin Cüreoglu, Murat Akkus, Üstün Osma, Mehmet Yaldiz, Faruk Oktay, Belgin Can, Cengiz Güven, Muhammet Tekin, and Faruk Meriç (2002), "The effect of benzalkonium chloride an electron microscopy study," *Eur Arch Otorhinolaryngol* 259: 362-364.

The surfactant compositions of the invention are typically present at a level of from about 0.01% to 20% by weight. More preferred levels of incorporation are from about 0.01% to 5% by weight, from about 0.01% to 2% by weight, from about 0.01% to 1%, most preferably from about 0.01% to 0.125% by weight. The surfactant is preferably formulated to be compatible with other components present in the composition. In liquid, or gel, or capsule, or injectable, or spray compositions the surfactant is most preferably formulated such that it promotes, or at least does not degrade, the stability of any protein or enzyme in these compositions. Further, the invention optimizes the concentration by keeping the concentration of absorption enhancer as low as possible, while still maintaining the desired effect.

The compositions of the invention when administered to the subject, yield enhanced mucosal delivery of the biologically active compound(s), or drug, with a peak concentration (or Cmax) of the compound(s) in a tissue, or fluid, or in a blood plasma of the subject that is about 15%, 20%, or 50% or greater as compared to a Cmax of the compound(s) in a tissue (e.g. CNS), or fluid, or blood plasma following intramuscular injection of an equivalent concentration of the compound(s) to the subject.

The measure of how much of the drug or compound(s) reaches the bloodstream in a set period of time, e.g. 24 hours can also be calculated by plotting drug blood concentration at various times during a 24-hour or longer period and then measuring the area under the curve (AUC) between 0 and 24 hours. Similarly, a measure of drug efficacy can also be determined from a time to maximal concentration (tmax) of the biologically active compound(s) in a tissue (e.g. CNS) or fluid or in the blood plasma of the subject between about 0.1 to 1.0 hours. The therapeutic compositions of the invention increase the speed of onset of drug action (i.e., reduce Tmax) by a factor of about 1.5-fold to 2-fold.

Also, the therapeutic compositions or formulations of the invention can be administered or delivered to a subject in need systemically or locally. Suitable routes may, for example, include oral, ocular, nasal, nasolacrimal, inhalation or pulmonary, oral cavity (sublingual or Buccal cell), transmucosal administration, vaginal, rectal, parenteral delivery, including intramuscular, subcutaneous, intravenous, intraperitoneal, or CSF delivery. Moreover, the mode of delivery e.g. liquid, gel, tablet, spray, etc. will also depend on the method of delivery to the subject.

Additionally, the therapeutic compositions of the invention can consist of a pharmaceutically acceptable carrier. A "pharmaceutically acceptable carrier" is an aqueous or non-aqueous agent, for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, and oils such as olive oil or injectable organic esters. A pharmaceutically acceptable carrier can contain physiologically acceptable compounds that act, for example, to stabilize or to increase the absorption of the specific inhibitor, for example, carbohydrates, such as glucose, sucrose or dextrans, antioxidants, such as ascorbic acid or glutathione, chelating agents, low molecular weight proteins or other stabilizers or excipients. A pharmaceutically acceptable carrier can also be selected from substances such as distilled water, benzyl alcohol, lactose, starches, talc, magnesium stearate, polyvinylpyrrolidone, alginic acid, colloidal silica, titanium dioxide, and flavoring agents.

Additionally, to decrease susceptibility of alkyl saccharides or saccharide alkyl esters to hydrolytic cleavage of the drug, various oxygen atoms within the drugs can be substituted for by sulfur (Defaye, J. and Gelas, J. in *Studies in Natural Product Chemistry* (Atta-ur-Rahman, ed.) Vol. 8, pp. 315-357, Elsevier, Amsterdam, 1991). For example, the heteroatom of the sugar ring can be either oxygen or sulfur, or the linkage between monosaccharides in an oligosaccharide can be oxygen or sulfur (Horton, D. and Wander, J. D., "Thio Sugars and Derivatives," The Carbohydrates: Chemistry and Biochemistry, 2d. Ed. Vol. IB, (W. Reyman and D. Horton eds.), pp. 799-842, (Academic Press, New York), (1972)). Oligosaccharides can have either $\alpha$ (alpha) or $\beta$ (beta) anomeric configuration (see Pacsu, E., et al. in Methods in Carbohydrate Chemistry (R. L. Whistler, et al., eds.) Vol. 2, pp. 376-385, Academic Press, New York 1963).

A composition of the invention can be prepared in tablet form by mixing a therapeutic agent or drug and one alkyl glycoside and/or saccharide alkyl ester according to the invention, and an appropriate pharmaceutical carrier or excipient, for example mannitol, corn starch, polyvinylpyrrolidone or the like, granulating the mixture and finally compressing it in the presence of a pharmaceutical carrier such as corn starch, magnesium stearate or the like. If necessary, the formulation thus prepared may include a sugar-coating or enteric coating or covered in such a way that the active principle is released gradually, for example, in the appropriate pH medium.

The term "enteric coating," is a polymer encasing, surrounding, or forming a layer, or membrane around the therapeutic composition or core. Also, the enteric coating can contain a drug which is compatible or incompatible with the coating. One tablet composition may include an enteric coating polymer with a compatible drug which dissolves or releases the drug at higher pH levels (e.g., pH greater than 4.0, greater than 4.5, greater than 5.0 or higher) and not at low pH levels (e.g., pH 4 or less); or the reverse.

In a preferred embodiment, the dose dependent release form of the invention is a tablet comprising:
(a) a core comprising:
  (i) a therapeutic agent or drug;
  (ii) a surfactant comprising at least one alkyl glycoside and/or saccharide alkyl ester; and
(b) at least one membrane coating surrounding the core, wherein the coating is an impermeable, permeable, semi-permeable or porous coating and becomes more permeable or porous upon contacting an aqueous environment of a defined pH.

The term "membrane" is synonymous with "coating," or equivalents thereof. The terms are used to identify a region of a medicament, for example, a tablet, that is impermeable, permeable, semi-permeable or porous to an aqueous solution(s) or bodily fluid(s), and/or to the therapeutic agent(s) or drug(s) encapsulated therein. If the membrane is permeable, semi-permeable or porous to the drug, the drug can be released through the openings or pores of the membrane in solution or in vivo. The porous membrane can be manufactured mechanically (e.g., drilling microscopic holes or pores in the membrane layer using a laser), or it can be imparted due to the physiochemical properties of the coating polymer(s). Membrane or coating polymers of the invention are well known in the art, and include cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, 4,036,228 and 4,11210 which are incorporated herein by reference.

Further, the enteric coating according to the invention can include a plasticizer, and a sufficient amount of sodium hydroxide (NaOH) to effect or adjust the pH of the suspension in solution or in vivo. Examples of plasticizers include tri-ethyl citrate, triacetin, tributyl sebecate, or polyethylene glycol. Other alkalizing agents, including potassium hydroxide, calcium carbonate, sodium carboxymethylcellulose, magnesium oxide, and magnesium hydroxide can also be used to effect or adjust the pH of the suspension in solution or in vivo.

Accordingly, in one embodiment, an enteric coating can be designed to release a certain percentage of a drug or drugs in certain mediums with a certain pH or pH range. For example, the therapeutic composition of the invention may include at least one enteric coating encasing or protecting at least one drug which is chemically unstable in an acidic environment (e.g., the stomach). The enteric coating protects the drug from the acidic environment (e.g., pH<3), while releasing the drug in locations which are less acidic, for example, regions of the small and large intestine where the pH is 3, or 4, or 5, or greater. A medicament of this nature will travel from one region of the gastrointestinal tract to the other, for example, it takes about 2 to about 4 hours for a drug to move from the stomach to the small intestine (duodenum, jejunum and ileum). During this passage or transit, the pH changes from about 3 (e.g., stomach) to 4, or 5, or to about a pH of 6 or 7 or greater. Thus, the enteric coating allows the core containing the drug to remain substantially intact, and prevents premature drug release or the acid from penetrating and de-stabilizing the drug.

Examples of suitable enteric polymers include but are not limited to cellulose acetate phthalate, hydroxypropylmethyl-cellulose phthalate, polyvinylacetate phthalate, methacrylic acid copolymer, shellac, cellulose acetate trimellitate, hydroxypropylmethylcellulose acetate succinate, hydroxypropylmethylcellulose phthalate, cellulose acetate phthalate, cellulose acetate succinate, cellulose acetate malate, cellulose benzoate phthalate, cellulose propionate phthalate, methylcellulose phthalate, carboxymethylethylcellulose, ethylhydroxyethylcellulose phthalate, shellac, styrene-acrylic acid copolymer, methyl acrylate-acrylic acid copolymer, methyl acrylate-methacrylic acid copolymer, butyl acrylate-styrene-acrylic acid copolymer, methacrylic acid-methyl methacrylate copolymer, methacrylic acid-ethyl acrylate copolymer, methyl acrylate-methacrylic acid-octyl acrylate copolymer, vinyl acetate-maleic acid anhydride copolymer, styrene-maleic acid anhydride copolymer, styrene-maleic acid monoester copolymer, vinyl methyl ether-maleic acid anhydride copolymer, ethylene-maleic acid anhydride copolymer, vinyl butyl ether-maleic acid anhydride copolymer, acrylonitrile-methyl acrylate-maleic acid anhydride copolymer, butyl acrylate-styrene-maleic acid anhydride copolymer, polyvinyl alcohol phthalate, polyvinyl acetal phthalate, polyvinyl butylate phthalate and polyvinyl acetoacetal phthalate, or combinations thereof. One skilled in the art will appreciate that other hydrophilic, hydrophobic and enteric coating polymers may be readily employed, singly or in any combination, as all or part of a coating according to the invention.

The therapeutic compositions of the invention in the form of a tablet can have a plurality of coatings, for example, a hydrophilic coating (e.g., hydroxypropylmethyl-cellulose), and/or a hydrophobic coating (e.g., alkylcelluloses), and/or an enteric coating. For example, the tablet core can be encases by a plurality of the same type of coating, or a plurality of different types of coating selected from a hydrophilic, hydrophobic or enteric coating. Hence, it is anticipated that a tablet can be designed having at least one, but can have more than one layer consisting of the same or different coatings dependent on the target tissue or purpose of the drug or drugs. For example the tablet core layer may have a first composition enclosed by a first coating layer (e.g. hydrophilic, hydrophobic, or enteri-coating), and a second same or different composition or drug having the same or different dosage can be enclosed in second coating layer, etc. This layering of various coatings provides for a first, second, third, or more gradual or dose dependent release of the same or different drug containing composition.

In a preferred embodiment, a first dosage of a first composition of the invention is contained in a tablet core and with an enteric-coating such that the enteric-coating protects and prevents the composition contained therein from breaking down or being released into the stomach. In another example, the first loading dose of the therapeutic composition is included in the first layer and consists of from about 10% to about 40% of the total amount of the total composition included in the formulation or tablet. In a second loading dose, another percentage of the total dose of the composition is released. The invention contemplates as many time release doses as is necessary in a treatment regimen. Thus, in certain aspects, a single coating or plurality of coating layers is in an amount ranging from about 2% to 6% by weight, preferably about 2% to about 5%, even more preferably from about 2% to about 3% by weight of the coated unit dosage form.

Accordingly, the composition preparations of the invention make it possible for contents of a hard capsule or tablet to be selectively released at a desired site the more distal parts of the gastro-intestinal tract (e.g. small and large intestine) by selecting the a suitable pH-soluble polymer for a specific region. Mechanical expulsion of the composition preparations may also be achieved by inclusion of a water absorbing polymer that expands upon water absorption within a hard semi-permeable capsule thus expelling composition through an opening in the hard capsule.

Drugs particularly suited for dose dependent time release include but are not limited to insulin like growth factor-I (IGF-I), somatomedin-C (SM-C; diabetes, nerve function, renal function), insulin (diabetes), calcitonin (osteoporosis), leptin (obesity; infertility), leptin derived short peptide (OB-3), hGH (AIDs wasting, dwarfism), human parathyroid hormone (PTH) (osteoporosis), melatonin (sleep), GLP-1 or Glucagon-like peptide-1 (diabetes), GiP (diabetes), pituitary adenylate cyclase-activating polypeptide (PACAP) and islet function (diabetes), GM-1 ganglioside, (Alzheimers), nerve growth factor (NGF), (Alzheimers), nafarelin (endometriosis), Synarel® (nafarelin acetate nasal solution), (D-tryp6)-LHRH (fertility), FGF (duodenal ulcer, macular degeneration, burns, wounds, spinal cord injuries, repair of bone and cartilage damage), VEGF antagonists (to block the receptor), VEGF (agonist) neonatal distress syndrome; ALS), leuprolide (prostate and breast cancer), interferon-alpha (chronic hepatitis C), low molecular weight heparin (blood clotting, deep vein thrombosis), PYY (obesity), LHRH antagonists (fertility), LH (luteinizing hormone), ghrelin antagonists (obesity), KGF (Parkinson's), GDNF (Parkinsons), G-CSF (erythropoiesis in cancer), Imitrex (migraine), Integrelin (anticoagulation), Natrecor® (congestive heart failure), human B-type natriuretic peptide (hBNP), SYNAREL® (Searl; nafarelin acetate nasal solution), Sandostatin (growth hormone replacement), Forteo (osteoporosis), DDAVP® Nasal Spray (desmopressin acetate), Cetrotide® (cetrorelix acetate for injection), Antagon™ (ganirelix acetate), Angiomax (bivalirudin; thrombin inhibitor), Accolate® (zafirlukast; injectable), Exendin-4 (Exanatide; diabetes), SYMLIN® (pramlintide acetate; synthetic amylin; diabetes), desmopressin, glucagon, ACTH (corticotrophin), C-peptide of insulin, GHRH and analogs (GnRHa), growth hormone releasing hormone, oxytocin, corticotropin releasing hormone (CRH), atrial natriuretic peptide (ANP), thyroxine releasing hormone (TRHrh), follicle stimulating hormone (FSH), prolactin, tobramycin ocular (corneal infections), Vasopressin, desmopresin, Fuzeon (Roche; HIV fusion inhibitor MW 4492), and Eptifibatide.

Further, it will be understood by one skilled in the art, that the specific dose level and frequency of dosage for any particular subject in need of treatment may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

It has been shown that alkyl glycosides, particularly alkylmaltosides and more specifically, dodecylmaltoside (DDM) and tetradecylmaltoside (TDM), stabilize insulin in solution and prevent aggregation of the peptide. Hovgaard et al., "Insulin Stabilization and GI absorption," *J. Control. Rel.*, 19 (1992) 458-463, cited in Hovgaard et al., "Stabilization of insulin by alkylmaltosides: A spectroscopic evaluation," *Int. J. Pharmaceutics* 132 (1996) 107-113 (hereinafter, "Hovgaard-1"). Further, Hovgaard-1 shows that even after 57 days, the DDM-insulin complex remained stable and possessed nearly full biological activity. It is postulated that the stability of the complex is due to the length of the alkyl group (number of carbon atoms) and the higher ratio of DDM to insulin ratio the better (e.g. 4:1 and 16:1; see FIG. 1 in Hovgaard 1). However, according to Hovgaard-1, although the DDM-insulin complex was stable, the same stability was not shown for other maltosides. Yet, in a related study, Hovgaard et al. (1996) demonstrated that when DDM-insulin was orally administered to animals in vivo, bioavailability of the complex was weak (e.g. 0.5%-1% bioavailability). Hovgaard et al., "Stabilization of insulin by alkylmaltoside. B. Oral absorption in vivo in rats," *Int. J. Pharmaceutics* 132 (1996) 115-121 (Hovgaard-2). Hence, an improved aspect of the invention is that the surfactant increases the bioavailability of a drug to the target tissues, organs, system etc., as well as increase drug stability.

Accordingly, one aspect of the invention is to provide therapeutic compositions having at least one drug and one surfactant, wherein the surfactant further consists of at least one alkyl glycoside and/or saccharide alkyl ester formulation which enhances the bioavailability of the drug. Determining the bioavailability of drug formulations is described herein. As used herein, "bioavailability" is the rate and extent to which the active substance, or moiety, which reaches the systemic circulation as an intact drug. The bioavailability of any drug will depend on how well is adsorbed and how much of it escapes being removed from the liver.

To determine absolute bioavailability, the tested drug and mode of administration is measured against an intravenous reference dose. The bioavailability of the intravenous dose is 100% by definition. For example, animals or volunteering humans are given an intravenous injections and corresponding oral doses of a drug. Urinary or plasma samples are taken over a period of time and levels of the drug over that period of time are determined.

The areas under the curve (AUC), of the plasma drug concentration versus time curves, are plotted for both the intravenous and the oral doses, and calculation of the bioavailability of both formulations is by simple proportion. For example, if the same intravenous and oral doses are given, and the oral AUC is 50% of the intravenous AUC, the bioavailability of the oral formulation is 50%. Note that the bioavailability of any drug is due to many factors including incomplete absorption, first pass clearance or a combination of these (discussed more below). Further, the peak concentration (or $C_{max}$) of the plasma drug concentration is also measured to the peak concentration ($C_{max}$) of the plasma drug concentration following intramuscular (IM) injection of an equivalent concentration the drug. Moreover, the time to maximal concentration (or $t_{max}$) of the plasma drug is about 0.1 to 1.0 hours.

To determine the relative bioavailability of more than one formulation of a drug (e.g. an alkyl glycoside or saccharide alkyl ester drug formulation), bioavailability of the formulations are assessed against each other as one or both drugs could be subject to first pass clearance (discussed more below) and thus undetected. For example, a first oral formulation is assessed against a second oral formulation. The second formulation is used as a reference to assess the bioavailability of the first. This type of study provides a measure of the relative performance of two formulations in getting a drug absorbed.

Bioavailabilities of drugs are inconsistent and vary greatly from one drug to the next. For example, the bioavailability of MIACALCIN® (salmon calcitonin from Novartis) nasal spray, a prescription medication for the treatment of postmenopausal osteoporosis in women, has a mean bioavailability of about 3% (range is 0.3%-30.6%; see FIG. 1). The MIACALCIN® product information sheet can be found on the world wide web at miacalcin.com/info/howWorks/index.jsp and drugs.com/PDR/Miacalcin_Nasal_Spray.html. The data on MIACALCIN®, which was obtained by various investigators using different methods and human subjects, show great variability in the drug's bioavailability, e.g. in normal volunteers only ~3% of the nasally administered dose is bioavailable, as compared to the same dose administered by intramuscular injection (MIACALCIN® product insert). This represents two orders of a magnitude in variability and is undesirable to the consumer.

Poor bioavailability of a drug can also be observed in NASCOBAL® (Nastech), or cyanocobalamin, which is used for the treatment and maintenance of the hematologic status of patients who are in remission following intramuscular vitamin $B_{12}$ therapies. The gel formulation was administered intranasally and the bioavailability of $B_{12}$ was compared to intramuscular $B_{12}$ injections. The peak concentrations of $B_{12}$ (or the Tmax) was reached in 1-2 hours after intranasal administration, and relative to the intramuscular injection, the bioavailability of $B_{12}$ nasal gel was found to be about 8.9% (90% confidence intervals, 7.1% to 11.2%).

The alkyl glycosides or sucrose esters of the present invention include any compounds now known or later discovered. Drugs which are particularly well suited for admixture with the alkyl glycosides and/or saccharide alkyl esters of the invention are those that are difficult to administer by other methods, e.g. drugs that are degraded in the gastrointestinal (GI) tract or those that are not absorbed well from the GI tract, or drugs that can be self-administered via the ocular, nasal, nasolacrimal, inhalation, or CSF delivery route instead of traditional methods such as injection. Some specific examples include peptides, polypeptides, proteins, nucleic acids and other macromolecules, for example, peptide hormones, such as insulin and calcitonin, enkephalins, glucagon and hypoglycemic agents such as tolbutamide and glyburide, and agents which are poorly absorbed by enteral routes, such as griseofulvin, an antifungal agent. Other compounds include, for example, nicotine, interferon (e.g., alpha, beta, gamma), PYY, GLP-1, synthetic exendin-4 (Exenatide), parathyroid hormone, and human growth hormone or other low molecular weight peptides and proteins.

Alternatively, bioavailability of a drug can be determined by measuring the levels of the drug's first pass clearance by the liver. Alkyl glycosides and/or saccharide alkyl ester compositions of the invention administered intranasally or via oral cavity (sublingual or Buccal cell) do not enter the hepatic portal blood system, thereby avoiding first pass clearance by the liver. Avoiding first past clearance of these formulations by the liver is described herein. The term, "first pass liver clearance" is the extent to which the drug is removed by the liver during its first passage in the portal blood through the liver to the systemic circulation. This is also called first pass metabolism or first pass extraction.

The two major routes of drug elimination from the body are excretion by the kidneys whereby the drug is unchanged; and elimination by the liver, whereby the drug is metabolized. The balance between these two routes depends on the relative efficiency of the two processes. The present invention describes herein elimination by the liver or liver clearance. First pass liver clearance is described by Birkett et al (1990 and 1991), which is incorporated by reference in its entirety. Birkett et al., *Aust Prescr,* 13 (1990):88-9; and Birkett et al., *Austra Prescr* 14:14-16 (1991).

Blood carrying drug from the systemic circulation enter the liver via the portal vein, and the liver in turn extracts a certain percentage or ratio (i.e. 0.5 or 50%) of that drug. The remainder left over (i.e. 0.2 or 20%) re-enters the systemic circulation via the hepatic vein. This rate of clearance of the drug is called the hepatic extraction ratio. It is the fraction of the drug in the blood which is irreversibly removed (or extracted) during the first pass of the blood through the liver. If no drug is extracted, the hepatic extraction ratio is zero. Conversely, if the drug is highly extracted in the first pass through the liver, the hepatic extraction ratio may be as high as 100% or 1.0. In general, clearance of the drug by the liver depends then on the rate of delivery of that drug to the liver (or the hepatic blood flow), and on the efficiency of removal of that drug (or the extraction ratio).

Therefore, the net equation used to determine hepatic clearance is:

$$\text{(hepatic clearance-blood flow)} = \text{(unbound fraction*intrinsic clearance)/blood flow+(unbound fraction*intrinsic clearance)} \quad (1)$$

The "unbound fraction" of drug is dependent on how tightly the drug is bound to proteins and cells in the blood. In general, it is only this unbound (or free) drug which is available for diffusion from the blood into the liver cell. In the absence of hepatic blood flow and protein binding, the "intrinsic clearance" is the ability of the liver to remove (or metabolize) that drug. In biochemical terms, it is a measure of liver enzyme activity for a particular drug substrate. Again, although intrinsic clearance can be high, drugs cannot be cleared more rapidly than that presented to the liver. In simple terms, there are two situations: where liver enzyme activity is very high or very low (i.e. high extraction ratio or low extraction ratio).

When liver enzyme activity is low, the equation simplifies to:

$$\text{hepatic clearance} = \text{unbound fraction*intrinsic clearance} \quad (2)$$

Clearance then is independent of blood flow, but instead depends directly on the degree of protein binding in the blood and the activity of drug metabolizing enzymes towards that drug.

In contrast, when liver enzyme activity is high, the equation is:

$$\text{hepatic clearance} = \text{liver blood flow} \quad (3)$$

In this scenario, because the enzymes are so active the liver removes most of the drug presented to it and the extraction ratio is high. Thus, the only factor determining the actual hepatic clearance is the rate of supply of drug to the liver (or hepatic blood flow).

First pass liver clearance is important because even small changes in the extraction of drugs can cause large changes in bioavailability. For example, if the bioavailability of drug A by oral administration is 20% by the time it reaches the systemic circulation, and the same drug A by intravenous administration is 100%, absent no other complicating factors, the oral dose will therefore have to be 5 times the intravenous dose to achieve similar plasma concentrations.

Secondly, in some instances where liver enzyme activity is very high, drug formulations should be designed to have the drug pass directly through to the systemic circulation and avoid first pass liver clearance all together. For example, drugs administered intranasally, sublingual, buccal, rectal, vagina, etc. directly enter the systemic circulation and do not enter the hepatic portal blood circulation to be partially or fully extracted by the liver. Alternatively, where drugs cannot be administered by the above means, a tablet with at least one enteric-coating layer to prevent release of the drug in the stomach (i.e. highly acidic environment) is provided. Thus, an objective of the invention is to administer drugs using these alternative routes.

Additionally, first pass liver clearance is an important factor because many patients are on more than one drug regimen, and this may cause drug interactions which increase or decrease liver enzyme activity; thereby increasing or decreasing metabolism (increasing or decreasing the hepatic extraction ratio) of the drug of interest.

Hence, therapeutic compositions of the invention can be administered directly to the systemic circulatory system and avoid first pass liver clearance. Avoiding first pass clearance assures that more of the drug will be available to the system. Stated another way, by avoiding first pass liver clearance, the bioavailability of the drug is increased.

The present invention also relates to methods of increasing absorption of a low molecular compound into the circulatory system of a subject comprising administering via the oral, ocular, nasal, nasolacrimal, inhalation, or the CSF delivery route the compound and an absorption increasing amount of a suitable nontoxic, nonionic alkyl glycoside having a hydrophobic alkyl joined by a linkage to a hydrophilic saccharide.

The composition formulation is appropriately selected according to the administration route, such as oral administration (oral preparation), external administration (e.g., ointment), injection (preparations for injection), and mucosal administration (e.g., buccal and suppository) etc. For example, excipients (e.g., starch, lactose, crystalline cellulose, calcium lactate, magnesium aluminometasilicate and anhydrous silicate), disintegrators (e.g., carboxymethylcellulose and calcium carboxymethylcellulose), lubricants (e.g., magnesium stearate and talc), coating agents (e.g., hydroxyethylcellulose), and flavoring agents can be used for oral and mucosal formulations; whereas, solubilizers and auxiliary solubilizers capable of forming aqueous injections (e.g., distilled water for injection, physiological saline and propylene glycol), suspending agents (e.g., surfactant such as polysorbate 80), pH regulators (e.g., organic acid and metal salt thereof) and stabilizers are used for injections; and aqueous or oily solubilizers and auxiliary solubilizers (e.g., alcohols and fatty acid esters), tackifiers (e.g., carboxy vinyl polymer and polysaccharides) and emulsifiers (e.g., surfactant) are used for external agents. The drug and the alkyl glycoside can be admixed, mixed, or blended along with the above excipients, disintegrators, coating polymers, solubilizers, suspending agents, etc., prior to administration, or they can be administered sequentially, in either order. It is preferred that they be mixed prior to administration.

The term, "mucosal delivery-enhancing agent" includes agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of a compound(s) (e.g., biologically active compound). Enhancement of mucosal delivery can occur by any of a variety of mechanisms, including, for example, by increasing the diffusion, transport, persistence or stability of the compound, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junction physiology, reducing the viscosity of mucus overlying the mucosal epithelium, reducing mucociliary clearance rates, and other mechanisms.

Exemplary mucosal delivery enhancing agents include the following agents and any combinations thereof:
(a) an aggregation inhibitory agent;
(b) a charge-modifying agent;
(c) a pH control agent;
(d) a degradative enzyme inhibitory agent;
(e) a mucolytic or mucus clearing agent;
(f) a ciliostatic agent;
(g) a membrane penetration-enhancing agent selected from:
(i) a surfactant; (ii) a bile salt; (ii) a phospholipid additive, mixed micelle, liposome, or carrier; (iii) an alcohol; (iv) an enamine; (v) an NO donor compound; (vi) a long-chain amphipathic molecule; (vii) a small hydrophobic penetration enhancer; (viii) sodium or a salicylic acid derivative; (ix) a glycerol ester of acetoacetic acid; (x) a cyclodextrin or beta-cyclodextrin derivative; (xi) a medium-chain fatty acid; (xii) a chelating agent; (xiii) an amino acid or salt thereof; (xiv) an N-acetylamino acid or salt thereof; (xv) an enzyme degradative to a selected membrane component; (ix) an inhibitor of fatty acid synthesis; (x) an inhibitor of cholesterol synthesis; and (xi) any combination of the membrane penetration enhancing agents recited in (i)-(x);
(h) a modulatory agent of epithelial junction physiology;
(i) a vasodilator agent;
(j) a selective transport-enhancing agent; and
(k) a stabilizing delivery vehicle, carrier, mucoadhesive, support or complex-forming species with which the compound is effectively combined, associated, contained, encapsulated or bound resulting in stabilization of the compound for enhanced nasal mucosal delivery, wherein the formulation of the compound with the intranasal delivery-enhancing agents provides for increased bioavailability of the compound in a blood plasma of a subject.

Additional mucosal delivery-enhancing agents include, for example, citric acid, sodium citrate, propylene glycol, glycerin, ascorbic acid (e.g., L-ascorbic acid), sodium metabisulfite, ethylenediaminetetraacetic acid (EDTA) disodium, benzalkonium chloride, sodium hydroxide, and mixtures thereof. For example, EDTA or its salts (e.g., sodium or potassium) are employed in amounts ranging from about 0.01% to 2% by weight of the composition containing alkyl saccharide preservative.

Therapeutic agents or drugs of the present invention can be peptides or proteins, medically or diagnostically useful, of small to medium size, e.g. up to about 15 kD, 30 kD, 50 kD, 75 kD, etc., or a protein having between about 1-300 amino acids or more. The methods of the invention also anticipate the use of small molecules, for example, an organic compound that has a molecular weight of less than 3 kD, or less than 1.5 kD.

The mechanisms of improved drug absorption according to the invention are generally applicable and should apply to all such peptides or protein, although the degree to which their absorption is improved may vary according to the molecular weight (MW) and the physicochemical properties of the peptide or protein, and the particular enhancer used. Examples of peptides or protein include vasopressin, vasopressin polypeptide analogs, desmopressin, glucagon, corticotropin (ACTH), gonadotropin, calcitonin, C-peptide of insulin, parathyroid hormone (PTH), growth hormone (HG), human growth hormone (hGH), growth hormone releasing hormone (GHRH), oxytocin, corticotropin releasing hormone (CRH), somatostatin or somatostatin polypeptide analogs, gonadotropin agonist or gonadotrophin agonist polypeptide analogs, human atrial natriuretic peptide (ANP), human thyroxine releasing hormone (TRH), follicle stimulating hormone (FSH), and prolactin.

One preferred composition of the invention is the peptide drug is Exenatide (or exendin-4) and an alkyl glycoside. Exenatide is a synthetic version of exendin-4, and has been used in clinical trials by Amylin™ Pharmaceuticals. Exendin-4 is a low molecular weight peptide that is the first of a new class of therapeutic medications known as incretin mimetic agents or hormones. Incretin hormones are any of various gastrointestinal (GI) hormones and factors that act as potent stimulators of insulin secretion, e.g. as gastric inhibitory polypeptide (GIP), glucagon-like peptide-1 (GLP-1), or Exenatide, or exendin-4, or equivalents thereof.

Exendin-4 is a naturally occurring 39-amino acid peptide isolated from salivary secretions of the Gila Monster Lizard. Eng et al., "Isolation and characterization of exendin-4, an exendin-3 analogue, from Heloderma suspectum venom. Further evidence for an exendin receptor on dispersed acini from guinea pig pancreas," *J. Biol. Chem.* 267(15):7402-7405 (1992). Exenatide exhibits similar glucose lowering actions to glucagons like peptide, or GLP-1. Exenatide is being investigated for its potential to address important unmet medical needs of many people with type 2 diabetes. Clinical trials suggest that Exenatide treatment decreases blood glucose toward target levels and is associated with weight loss. The effects on glucose control observed with Exenatide treatment are likely due to several actions that are similar to those of the naturally occurring incretin hormone GLP-1 (see Example 7). These actions include stimulating the body's ability to produce insulin in response to elevated levels of blood glucose, inhibiting the release of glucagon following meals and slowing the rate at which nutrients are absorbed into the bloodstream. In animal studies Exenatide administration resulted in preservation and formation of new beta cells, the insulin-producing cells in the pancreas, which fail as type 2 diabetes progresses.

Use of Exenatide, incretin mimetic agents or equivalents thereof can be used to treat various forms of diabetes including but not limited to brittle diabetes, chemical diabetes or impaired glucose tolerance, gestational diabetes, diabetes insipidus, diabetes insipidus central, diabetes insipidus nephrogenic, diabetes insipidus pituitary, latent diabetes, lipatrophic diabetes, maturity-onset diabetes of youth (MODY), diabetes mellitus (DM), diabetes mellitus adult-onset (type 2 DM), diabetes mellitus insulin-dependent (IDDM, or type 1 DM), diabetes mellitus non-insulin dependent (NIDDM), diabetes mellitus juvenile or juvenile-onset, diabetes mellitus ketosis-prone, diabetes mellitus ketosis-resistant, diabetes mellitus malnutrition-related (MRDM), diabetes mellitus tropical or tropical pancreatic, diabetes mellitus, preclinical diabetes, or diabetes induced by various drugs e.g. thiazide diabetes, steroid diabetes, or various diabetes animal model including but not limited to alloxan diabetes and puncture diabetes.

In another aspect, therapeutic compositions of the invention are used to treat obesity. Obesity is a common problem in both adults and adolescents. For example, PYY3-36 (or AC162352) is a hormone that plays a critical role in decreasing appetites. The gut hormone fragment peptide PYY3-36 (PYY) reduces appetite and food intake when infused into subjects of normal weight. Similar to the adipocyte hormone, leptin, PYY reduces food intake by modulating appetite circuits in the hypothalamus. However, in obese patients there is a resistance to the action of leptin, thereby limiting leptin's therapeutic effectiveness. Still other studies show that PYY reduces food intake. Injection of PYY revealed that they eat on average 30% less than usual, resulting in weight loss. Hence, PYY 3-36 has potential as a treatment for obesity. Amylin™ Pharmaceuticals submitted an Investigational New Drug application for PYY 3-36 in 2003.

Compounds whose absorption can be increased by the method of this invention include any compounds now known or later discovered, in particular drugs, or therapeutic compounds, molecules or agents that are difficult to administer by other methods, for example, drugs that are degraded in the gastrointestinal (GI) tract or that are not absorbed well from the GI tract, or drugs that subjects could administer to themselves more readily via the ocular, nasal, nasolacrimal, inhalation or pulmonary, oral cavity (sublingual or Buccal cell), or CSF delivery route than by traditional self-administration methods such as injection. Some specific examples include peptides, polypeptides, proteins and other macromolecules, for example, peptide hormones, such as insulin and calcitonin, enkephalins, glucagon and hypoglycemic agents such as tolbutamide and glyburide, and agents which are poorly absorbed by enteral routes, such as griseofulvin, an antifungal agent. Other compounds include, for example, nicotine, interferon (e.g., alpha, beta, gamma), PYY, GLP-1, synthetic exendin-4 (Exenatide), parathyroid hormone (PTH), and human growth hormone or other low molecular weight peptides and proteins.

Further, the therapeutic compositions of the invention also contemplate non-peptide drugs or therapeutic agents. For example, in U.S. Pat. No. 5,552,534, non-peptide compounds are disclosed which mimic or inhibit the chemical and/or biological activity of a variety of peptides. Such compounds can be produced by appending to certain core species, such as the tetrahydropyranyl ring, chemical functional groups which cause the compounds to be at least partially cross-reactive with the peptide. As will be recognized, compounds which mimic or inhibit peptides are to varying degrees cross-reactivity therewith. Other techniques for preparing peptidomimetics are disclosed in U.S. Pat. Nos. 5,550,251 and 5,288,707. The above U.S. patents are incorporated by reference in their entirety.

The method of the invention can also include the administration, along with the alkyl glycoside and a protein or peptide, a protease or peptidase inhibitor, such as aprotinin, bestatin, alpha$_1$, proteinase inhibitor, soybean trypsin inhibitor, recombinant secretory leucocyte protease inhibitor, captopril and other angiotensin converting enzyme (ACE) inhibitors and thiorphan, to aid the protein or peptide in reaching its site of activity in the body in an active state (i.e., with degradation minimal enough that the protein is still able to function properly). The protease or peptidase inhibitor can be mixed with the alkyl glycoside and drug and then administered, or it can be administered separately, either prior to or after administration of the glycoside or drug.

The invention also provides a method of lowering blood glucose level in a subject comprising administering a blood glucose-reducing amount of a composition comprising insulin and an absorption increasing amount of a suitable non-toxic, nonionic alkyl glycoside having a hydrophobic alkyl group joined by a linkage to a hydrophilic saccharide, thereby increasing the absorption of insulin and lowering the level of blood glucose. A "blood glucose-reducing amount" of such a composition is that amount capable of producing the effect of reducing blood glucose levels, as taught herein. Preferred is an amount that decreases blood glucose to normoglycemic or near normoglycemic range. Also preferred is an amount that causes a sustained reduction in blood glucose levels. Even more preferred is an amount sufficient to treat diabetes, including diabetes mellitus (DM) by lowering blood glucose level. Thus, the instant method can be used to treat diabetes mellitus. Preferred alkyl glycosides are the same as those described above and exemplified in the Examples.

Also provided is a method of raising blood glucose level in a subject by administering a blood glucose-raising amount comprising glucagons and at least one alkyl glycoside and/or saccharide alkyl ester. When the composition includes insulin, it can be used to cause the known effect of insulin in the bloodstream, i.e., lower the blood glucose levels in a subject. Such administration can be used to treat diabetes mellitus, or related diseases. A "blood glucose-raising amount" of glucagon in such a composition is that amount capable of producing the effect of raising blood glucose levels. A preferred amount is that which increases blood glucose to normoglycemic or near-normoglycemic range. Another preferable amount is that which causes a sustained rising of blood glucose levels. Even more preferred, is that amount which is sufficient to treat hypoglycemia by raising blood glucose level. Thus, this method can be used to treat hypoglycemia. Preferred alkyl glycosides are the same as those described above and exemplified in the Examples.

Similarly, when this composition includes glucagon, it can be used to cause the known effect of glucagon in the bloodstream, i.e., to raise the blood glucose levels in a subject. Such administration can therefore be used to treat hypoglycemia, including hypoglycemic crisis.

The invention also provides methods for ameliorating neurological disorders which comprises administering a therapeutic agent to the cerebral spinal fluid (CSF). The term "neurological disorder" denotes any disorder which is present in the brain, spinal column, and related tissues, such as the meninges, which are responsive to an appropriate therapeutic agent. The surprising ability of therapeutic agents of the present invention to ameliorate the neurological disorder is due to the presentation of the therapeutic agent to persist in the cerebro-ventricular space. The ability of the method of the invention to allow the therapeutic agent to persist in the region of the neurological disorder provides a particularly effective means for treating those disorders.

It will be understood, however, that the specific dose level and frequency of dosage for any particular subject in need of treatment may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. Generally, however, dosage will approximate that which is typical for known methods of administration of the specific compound. For example, for intranasal administration of insulin, an approximate dosage would be about 0.5 unit/kg regular porcine insulin (Moses et al.). Dosage for compounds affecting blood glucose levels optimally would be that required to achieve proper glucose levels, for example, to a normal range of about 5-6.7 mM. Additionally, an appropriate amount may be determined by one of ordinary skill in the art using only routine testing given the teachings herein (see Examples).

Furthermore, the compositions of the invention can be administered in a format selected from the group consisting of a drop, a spray, an aerosol and a sustained release format. The spray and the aerosol can be achieved through use of the appropriate dispenser. The sustained release format can be an ocular insert, erodible microparticulates, swelling mucoadhesive particulates, pH sensitive microparticulates, nanoparticles/latex systems, ion-exchange resins and other polymeric gels and implants (Ocusert, Alza Corp., California; Joshi, A., S. Ping and K. J. Himmelstein, Patent Application WO 91/19481). These systems maintain prolonged drug contact with the absorptive surface preventing washout and nonproductive drug loss.

The present invention is more particularly described in the following examples which are intended as illustrative only since numerous modifications and variations therein will be apparent to those skilled in the art. The following examples are intended to illustrate but not limit the invention.

EXAMPLE 1

Alkyl Glycoside and/or Sucrose Ester Formulations do not Cause Mucosa Irritation or Disruption The nasal mucosa is highly vascularized and hence optimal for high drug permeation. Moreover, absorption of drug(s) through the nasal mucosa is available to the central nervous system (CNS). Although local application of drugs is desirable, a challenge for this method of administration is mucosal irritancy.

A formulation consisting of an alkyl glycoside (0.125% TDM) in a commercial over-the-counter (OTC) nasal saline was administered in vivo to human nasal epithelium over a period of over one month. The 0.125% TDM formulation is compared to the control, namely the same commercial (OTC) nasal saline, over the same period of time. Results show that during and after 33 days of daily TDM administration (i.e., the duration of the study), there is no observable irritation of the nasal mucosa (data not shown). Thus, compositions of the invention are non-toxic and non-irritable providing repeated and long-term intranasal administration, which is beneficial for those patients with chronic and ongoing disease(s).

A similar test was performed using sucrose dodecanoate, a sucrose ester. Sucrose dodecanoate is administered in vivo to human nasal epithelium and during and after 47 days (i.e., the duration of the study), no observable irritation was detected (data not shown). Thus, these results show that alkyl glycosides and sucrose esters of the invention are non-toxic and do not cause mucosa irritation when administered daily over a long period of time.

EXAMPLE 2

Alkyl Glycoside and/or Sucrose Ester Compositions Stabilize Drugs by Increasing Drug Bioavailability and Reducing Drug Bioavailability Variance Stability of the alkyl glycoside depends, in part, on the number of carbon atoms or length of the alkyl chain and other long alkyl chains, with tetradecylmaltoside (TDM) having the greatest effect; but other highly branched alkyl chains including DDM also have stabilizing effects. In contrast to Hovgaard-1, which described the preference for a high alkyl glycoside to drug ratio, the instant invention shows that this ratio is much lower. For example, alkyl glycosides in the range of about 0.01% to about 6% by weight result in good stabilization of the drug; whereas Hovgaard-1 shows stabilization is only achieved at much higher ratios of alkyl glycosides to drug (10:1 and 16:1). Even more interesting, alkyl glycosides of the invention in the range of about 0.01% to about 6% have increased bioavailability (see FIG. 1). This is in sharp contrast to Hovgaard-2, which showed relatively low bioavailability (0.5-1%) at the high alkyl glycoside ratios (10:1 and 16:1).

FIG. 1 is a graph comparing the bioavailability of the drug MIACALCIN® (salmon calcitonin from Novartis) with and without alkyl glycoside (TDM). MIACALCIN® is a nasal spray and administered directly onto the nasal epithelium or nasal mucosa. FIG. 1 shows that MIACALCIN® minus alkyl glycoside has very low bioavailability levels in humans (MIACALCIN® product specification insert), as compared to the MIACALCIN® with alkyl glycoside as administered to rats. More specifically, intranasal delivery of MIACALCIN® with 0.125% and 0.250% alkyl glycoside (TDM) resulted in about 43% to about 90% bioavailability, respectively. The bioavailability of intranasal administration of MIACALCIN® without alkyl glycoside is only about 3% in humans, and was undetectable in rats, suggesting that the rat is a stringent model for estimating intranasal drug absorption in humans. Thus, the alkyl glycoside of the invention enhances absorption and increases bioavailability of the drug.

Furthermore, besides increasing the bioavailability of the drug, the alkyl glycoside compositions of the invention effectively decrease the bioavailability variance of the drug. FIG. 1 shows that administration of MIACALCIN® with alkyl glycoside (0.125% or 0.25%) intranasally has a bioavailability variance of +/−8%, whereas the bioavailability variance without alkyl glycoside is 0.3% to 30%, or a two orders of magnitude change. The increase in bioavailability and the decrease in the bioavailability variance ensures patient-to-patient variability is also reduced. The results as shown in FIG. 1 are administered intranasally, however, similar results are expected for oral, buccal, vaginal, rectal, etc. delivery and at different alkyl glycoside concentrations.

Thus, contrary to the art, the alkyl glycoside compositions of the invention, in the range of about 0.01% to about 6% result in increased bioavailability and reduced bioavailability variance. This has not otherwise been reported.

EXAMPLE 3

Ocular Administration of Alkyl Saccharides Plus Insulin Produces Hypoglycemic Effects In Vivo Normal rats were anesthetized with a mixture of xylazine/ketamine to elevate their blood glucose levels. The elevated levels of D-glucose that occur in response to anesthesia provide an optimal system to measure the systemic hypoglycemic action of drug administration, e.g. insulin-containing eye drops. This animal model mimics the hyperglycemic state seen in diabetic animals and humans. In the experimental animal group, anesthetized rats are given eye drops containing insulin. Blood glucose levels from the experimental group are compared to anesthetized animals which received eye drops without insulin. The change in blood glucose levels and the differential systemic responses reflects the effect of insulin absorbed via the route of administration, e.g. ocular route.

Adult male Sprague-Dawley rats (250-350 g) were fed ad libitum, and experiments were conducted between 10:00 a.m. and 3:00 p.m. Rats were anesthetized with a mixture of xylazine (7.5 mg/kg) and ketamine (50 mg/kg) given intraperitoneally (IP) and allowed to stabilize for 50-90 min before the administration of eye drops. Anesthesia of a normal rat with xylazine/ketamine produces an elevation in blood glucose values which provides an optimal state to determine the systemic hypoglycemic action of insulin-containing eye drops. Blood D-glucose values were measured by collecting a drop of blood from the tail vein at 5-10 min intervals throughout the experiment and applying the blood to glucometer strips (Chemstrip bG) according to directions provided with the instrument (Accu-Chek II, Boehringer Mannheim Diagnostics; Indianapolis, Ind.). Blood D-glucose values ranged from 200 to 400 mg/dl in anesthetized nondiabetic rats.

At time 0, after a 50-90 min stabilization period, rats were given 20 µl of eye drops composed of phosphate-buffered saline (PBS) with or without 0.2% regular porcine insulin and 0.125%-0.5% of the absorption enhancing alkyl glycoside (e.g. TDM) to be tested. Eye drops were instilled at time 0 using a plastic disposable pipette tip with the eyes held open, and the rat was kept in a horizontal position on a warming pad (37° C.) throughout the protocol. The rats were given additional anesthesia if they showed signs of awakening. Rats received in each eye 20 µl of 0.125-0.5% absorption enhancer in phosphate buffered saline, pH 7.4 with (experimental) or without (control) 0.2% (50 U/ml) regular porcine insulin (Squibb-Novo, Inc.) for a total of 2 U per animal. Octyl-β-D-maltoside, decyl-β-D-maltoside, dodecyl-µ-D-maltoside, tridecyl-β-D-maltoside and tetradecyl-β-D-maltoside were obtained from Anatrace, Inc. (Maumee, Ohio). Hexylglucopyranoside, heptylglucopyranoside, nonylglucopyranoside, decylsucrose and dodecylsucrose were obtained from Calbiochem, Inc. (San Diego, Calif.); Saponin, BL-9 and Brij 78 were obtained from Sigma Chemical Co. (St. Louis, Mo.).

The D-glucose levels in the blood remained elevated when the animals received eye drops containing: 1) saline only; 2) 0.2% regular porcine insulin in saline only; or 3) absorption enhancer only. However, when rats received eye drops containing 0.2% regular porcine insulin and several alkylmaltoside or alkylsucrose compounds, a pronounced decrease in blood D-glucose values occurred and was maintained for up to two hours. Insulin administered ocularly with 0.5% dodecyl-β-D-maltoside (see Table I) or 0.5% decyl-β-D-maltoside (see Table III) results in a prompt and sustained fall in blood glucose levels which are maintained in the normoglycemic (80-120 mg/dl) or near-normoglycemic (120-160 mg/dl) range for the two hour duration of the experiment. Hence, at least two alkylmaltosides are effective in achieving sufficient absorption of insulin delivered via the ocular route to produce a prompt and sustained fall in blood glucose levels in experimentally hyperglycemic animals. The surfactant compositions of the invention are therefore useful to achieve systemic absorption of insulin and other peptides/proteins, e.g., glucagon and macromolecular drugs and heparin delivered via the ocular route in the form of eye drops.

Several other alkylmaltosides are also effective as absorption enhancers for ocular administration of insulin including 0.5% tridecylmaltoside (see Table III) and 0.125% (Table II) and 0.5% tetradecyl maltoside. These studies show that alkylmaltosides with the longer alkyl chains (or number of carbon atoms), e.g., dodecyl-, tridecyl- and tetradecyl-β-D-maltosides, are more effective. The increase in the number of carbon atoms also contributes to the greater hydrophobic/hydrophilic structural balance and absorption enhancing effect. The shorter alkyl chains (fewer carbon atoms) e.g., decylmaltoside, or no, e.g., octylmaltoside, produce less absorption enhancing activity. It is noted that the most effective alkylmaltosides produce effects comparable to or greater than those seen with other absorption enhancers such as saponin, and with the added advantage that they can be metabolized to nontoxic products following systemic absorption.

The effects of the alkylmaltosides as absorption enhancers are dose-dependent, as can be seen by examining the effects of different concentrations ranging from 0.125-0.5% in producing a hypoglycemic effect when combined with insulin. Whereas, 0.5% and 0.375% dodecylmaltoside appear equally effective in achieving systemic absorption of insulin and reduction of blood glucose levels, 0.25% has a smaller and more transient effect and 0.125% is ineffective (Table I). Similarly, tridecylmaltoside also shows a dose-dependent effect in lowering blood glucose concentrations when combined with insulin, but the effect achieved with even 0.25% of the absorption enhance is sustained for the two hour time course of the experiment. Thus, dose-dependent effects of the alkylmaltosides suggest that they achieve enhancement of protein absorption via the ocular route in a graded fashion proportional to the concentration of the agent.

TABLE I

Effect of Eye Drops Containing Insulin Plus Various Concentrations of Dodecyl Maltoside on Blood Glucose Values (in mg/dl) in Rat

| | Dodecyl Maltoside Concentration | | | |
|---|---|---|---|---|
| | 0.125% | 0.25% | 0.375% | 0.50% |
| Time (min) | Blood Glucose Concentrations (mg/dl) | | | |
| −20 | 305 ± 60 | 271 ± 38 | 305 ± 51 | 375 ± 9 |
| −10 | 333 ± 58 | 295 ± 32 | 308 ± 27 | 366 ± 12 |
| 0 | 338 ± 67 | 323 ± 62 | 309 ± 32 | 379 ± 4 |

TABLE I-continued

Effect of Eye Drops Containing Insulin Plus
Various Concentrations of Dodecyl Maltoside
on Blood Glucose Values (in mg/dl) in Rat

| | Dodecyl Maltoside Concentration | | | |
|---|---|---|---|---|
| | 0.125% | 0.25% | 0.375% | 0.50% |
| Time (min) | Blood Glucose Concentrations (mg/dl) | | | |
| 30 | 349 ± 64 | 250 ± 48 | 212 ± 18 | 297 ± 18 |
| 60 | 318 ± 38 | 168 ± 22 | 134 ± 4 | 188 ± 25 |
| 90 | 325 ± 57 | 188 ± 55 | 125 ± 12 | 141 ± 13 |
| 120 | 342 ± 78 | 206 ± 63 | 119 ± 19 | 123 ± 5 |

The absorption enhancing effects of the alkyl saccharides were not confined to the alkylmaltosides alone since dodecylsucrose (0.125%, 0.25%, 0.375%) also shows a dose-dependent effect in producing ocular absorption of insulin and reduction in blood glucose levels. This effect is observed even at 0.125% alkyl saccharide (from 335 mg/dl.+−0.26 mg/dl at time 0 min. to 150 mg/dl+−0.44 mg/dl at time 120 min.). 0.5% decylsucrose was also effective in reducing blood glucose levels, but as shown for the alkylmaltosides, a reduction in the length of the alkyl chain, and hence the hydrophobic properties of the molecule, appears to reduce the potency of the alkylsucrose compounds. However, a significant and sustained reduction in blood glucose levels is achieved with 0.5% decylsucrose (from 313 mg/dl.+−0.15 mg/dl at time 0 min. to 164 mg/dl+−0.51 mg/dl at time 120 min.). The absorption enhancing abilities of alkyl saccharides with two distinct disaccharide moieties suggests that it is the physicochemical properties of the compounds which are crucial to their activity and that other alkyl saccharides, e.g., dodecyllactose, have the right balance of properties to be equally or more effective as absorption enhancers while retaining the metabolic and nontoxic properties of the alkylsaccharide enhancing agents. These alkyl saccharides are anticipated by the invention.

Studies with alkylglucosides were also conducted; 0.5% hexylglucoside and 0.5% heptylglucoside were ineffective at promoting insulin absorption from the eye, but 0.5% nonylglucoside effectively stimulated insulin absorption and reduced blood glucose levels (from 297 mg/dl to 150 mg/dl). This result once further supports that the alkyl chain length, as well as the carbohydrate moiety, play critical roles in effectively enhancing insulin absorption.

It should be noted that no damaging effects (i.e. non-irritants) to the ocular surface were observed with any of the alkylmaltoside or alkylsucrose agents employed in these studies. Furthermore, the prompt and sustained hypoglycemic effects produced by these agents in combination with insulin suggest that these absorption enhancers do not adversely affect the biological activity of the hormone, in keeping with their nondenaturing, mild surfactant properties.

Thus, therapeutic compositions on the invention consisting of at least an alkyl glycoside and a drug are stable and the alkyl glycosides enhance the absorption of the drug.

EXAMPLE 4

Ocular and Intranasal Administration of TDM Plus Glucagon Produces Hypoglycemic Effects In Vivo Since previous Examples showed that administration via eye drops of an absorption enhancer with drug e.g. insulin results in significant absorption of the drug via the nasolacrimal drainage system, therapeutically effective administration of insulin with alkylmaltosides, alkylsucrose and like agents by intranasal administration is tested herein.

Tetradecylmaltoside (TDM) in combination with insulin also produced a drop in blood D-glucose levels when administered in the form of a drop intranasally as well as via a drop by the ocular route. Eye drops containing 0.2% regular porcine insulin with 0.125% tetradecylmaltoside are administered to rats as previously described. The administration of the composition produces a prompt and prominent drop in blood glucose levels. The drop in blood glucose levels decrease even more by administration of a nose drop containing the same concentration of insulin with 0.5% tetradecylmaltoside (Table II). Thus, intranasal delivery and administration of the alkyl saccharide with drug results in lowering of blood glucose levels.

TABLE II

Effect of Insulin Eye Drops, Containing 0.125% Tetradecyl
Maltoside and Nose Drops Containing 0.5% Tetradecyl
Maltoside on Blood Glucose Values in Rats

| Time (min) | Blood Glucose (mg/dl) |
|---|---|
| −20 | 319 |
| −10 | 311 |
| Eye drops added | |
| 0 | 322 |
| 15 | 335 |
| 30 | 276 |
| 45 | 221 |
| 60 | 212 |
| 75 | 167 |
| 90 | 174 |
| 105 | 167 |
| 120 | 208 |
| Nose Drops Added | |
| 135 | 129 |
| 150 | 74 |
| 165 | 76 |
| 180 | 68 |

EXAMPLE 5

Ocular Administration of Alkyl Saccharides Plus Insulin Produces Hyperglycemic Effects In Vivo Previous studies demonstrated that insulin absorption from the eye is stimulated by saponin, BL-9 and Brij-78. BL-9 and Brij-78 are ineffective at stimulating the absorption of glucagon from the eye, whereas saponin is effective. Glucagon absorption from the eye was measured in rats given eye drops containing various surfactants plus glucagon (30 μg) (Eli Lilly, Indianapolis, Ind.) by monitoring an elevation in blood D-glucose levels. In these experiments, rats were anesthetized with sodium pentobarbital rather than xylazine/ketamin. This modification of the procedure resulted in basal blood glucose levels in the normoglycemic range and made it possible to readily monitor the hyperglycemic action of any glucagon absorbed from the eye.

Paired animals that receive eye drops containing the surfactant alone, or glucagon alone, were compared to animals receiving eye drops with the surfactant plus glucagon. When eyedrops containing 0.5% saponin plus glucagon are administered to rats, the level of D-glucose in blood rises significantly, but no such effect is observed with eye drops containing 0.5% BL-9 or 0.5% Brij-78 plus glucagon. Interestingly, when eye drops containing dodecylsucrose, decylmaltose or tridecylmaltose plus glucagon are administered to rats which were previously treated with eye drops containing these surfactant agents plus insulin, the glucagon is absorbed and blood D-glucose values increase significantly (Table III). This result confirms that ocular administration of certain alkylsaccharides can enhance the absorption of drugs, including glucagon and insulin. Moreover, it is now possible to treat for a hypoglycemic crisis using a formulation with at least an alkyl saccharide of the invention.

TABLE III

Effect of Eye Drops Containing Insulin or Glucagon and 0.5% Decyl Maltoside, 0.5% Dodecyl Sucrose, or 0.5% Tridecyl Maltoside on Blood Glucose Values in Rats

| Time (min) | Surfactant Agent | | |
|---|---|---|---|
| | Dodecyl Sucrose | Decyl Maltoside | Tridecyl Maltoside |
| | Blood Glucose Concentration (mg/dl) | | |
| −20 | 266 | 249 | 255 |
| −10 | 305 | 287 | 307 |
| Insulin Eye Drops Added | | | |
| 0 | 351 | 337 | 323 |
| 10 | 347 | 304 | 309 |
| 20 | 252 | 292 | 217 |
| 30 | 161 | 221 | 131 |
| 40 | 120 | 164 | 100 |
| 50 | 105 | 138 | 87 |
| 60 | 114 | 114 | 107 |
| 70 | 113 | 104 | 115 |
| 80 | 104 | 110 | 79 |
| 90 | 86 | 120 | 85 |
| 100 | 113 | 92 | 76 |
| 110 | 107 | 81 | 74 |
| 120 | 112 | 87 | 75 |
| Glucagon Eye Drops Added | | | |
| 130 | 111 | 95 | 82 |
| 140 | 143 | 99 | 121 |
| 150 | 202 | 132 | 148 |
| 160 | 247 | 157 | 173 |
| 170 | 242 | 171 | 162 |
| 180 | 234 | 180 | 162 |
| 190 | 211 | 189 | 156 |

EXAMPLE 6

Figure 2:
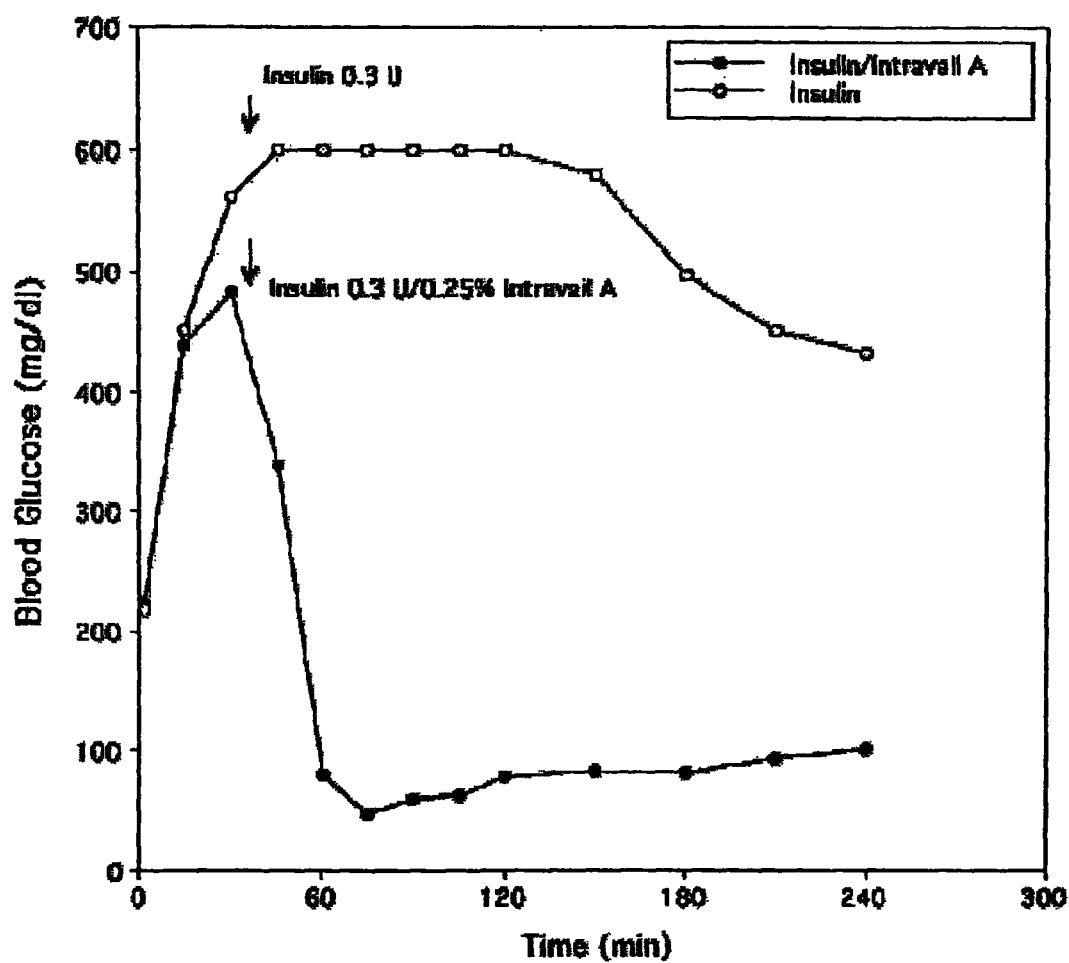
FIG. 2 is a graph showing the effect of intranasal administration of insulin/0.25% TDM (filled circles) and intranasal administration of insulin alone (open circles) in reducing blood glucose levels.

Intranasal Administration of 0.25% TDM Plus Insulin Decreases Blood Glucose Levels In Vivo Intranasal administration of drugs or agents are possible in animal models e.g. mice and rats, although the nasal opening in is very small. In the experiments and results described herein, an anesthesia-induced hyperglycemia model was used (described in Examples above). Hyperglycemic animals were induced by an intraperitoneal (IP) injection containing xylazine-ketamine and blood glucose levels were monitored over a period of time. Immediately after the xylazine-ketamine injection, there was an increase in the blood glucose levels as shown in FIG. 2 (closed dark circles), and blood glucose levels were about 450 mg/dl. The increase in blood glucose levels was attributed to the inhibition of pancreatic insulin secretion. Blood glucose levels peak to about 482 mg/dl by 30 minutes after the xylazine-ketamine injection (FIG. 2). Then, at approximately 33 minutes after the xylazine-ketamine injection, 6 μL of insulin (Humalog) in 0.25% tetradecylmaltoside (TDM; or Intravail A) was administered intranasally using a long thin micropipette tip, and blood glucose levels were monitored at about 15 minute intervals. After administration of the 0.25% TDM/insulin composition, there was a rapid decrease in blood glucose levels, reaching a low of about 80 mg/dl at about the 60 minute time point, or about 30 minutes after the insulin administration (FIG. 2). At about the 75 minute time point, blood glucose levels gradually returned to the baseline level in a normoglycemic mouse, or about 80-100 mg/dl.

The results above were compared with animals treated with insulin alone (same dosage), minus 0.25% TDM (FIG. 2, open circles). The insulin only treatment showed blood glucose levels do not start to decline until at about the 120 minute time mark, or about 110 minutes after the insulin administration. Further, the blood glucose levels observed in animals treated with insulin alone never return to normoglycemic levels, as was observed in those animals receiving insulin plus 0.25% TDM (FIG. 2).

Thus, these results again demonstrate that compositions of the invention consisting of certain alkyl glycosides or alkyl saccharides plus a drug, e.g. insulin, effectively lower blood glucose levels, and that these effects are measurable shortly after administration of the drug.

EXAMPLE 7

Figure 3:
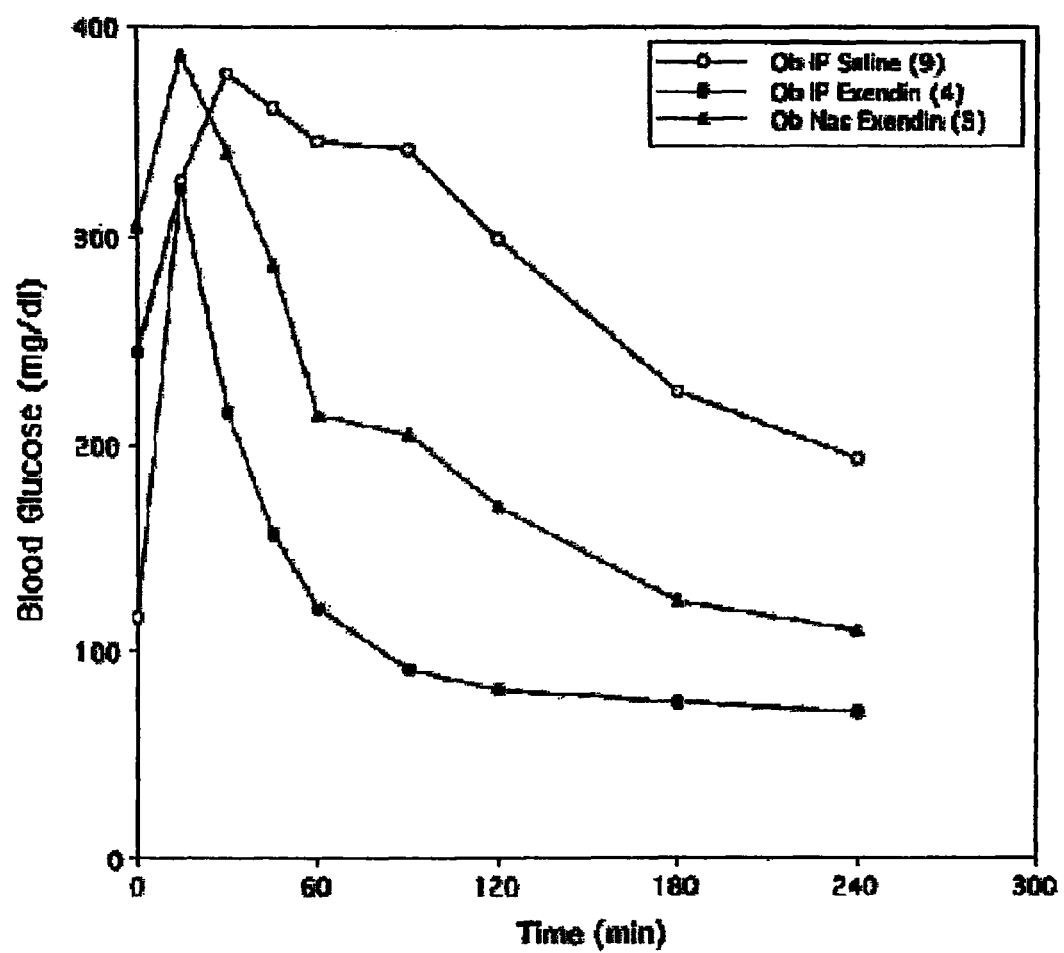
FIG. 3 is a graph showing the effect of intranasal (closed triangles) and intraperitoneal (IP) injection (closed circles) administration of exendin-4/0.25% TDM and IP injection of saline alone, minus TDM (open circles) in reducing blood glucose levels following intraperitoneal (IP) injection of glucose (i.e., in a so-called "glucose tolerance test").

Intranasal Administration of 0.25% TDM (Intravail A)+Exendin-4 Decreases Blood Glucose Levels In Vivo The ob/ob mouse model was utilized for the studies described herein. Friedman, J. M., Nature 404, 632-634 (2000). All animals received an intraperitoneal (IP) injection of a bolus of 2 g/kg glucose for purposes of determining glucose tolerance. At time 0 the experimental animals were given about 100 micrograms/kg of exendin-4/0.25% TDM (exendin-4 from American Peptide) either as 10 μl of nasal drops (FIG. 3; closed triangles), or by IP injection (FIG. 3; closed circles), or by and IP injection of saline alone (no drug, no TDM; FIG. 3; open circles). Control animals were previously performed and received no drugs. The results of this study are shown in FIG. 3.

FIG. 3 shows that glucose tolerance of the animals were different since blood glucose levels vary at time 0 when the animals received the glucose bolus. Regardless, of the glucose tolerance level at time 0, immediately after injection of the glucose bolus, blood glucose levels increased in all three animals. The blood glucose level of the animal receiving the IP injection of saline alone does not decrease as rapidly as the experimental animals receiving the drug. Moreover, the animal receiving the IP injection of saline alone never reached a normoglycemic level (FIG. 3, open circles). In contrast, the experimental animals, after administration of nasal drops of exendin-4/TDM, or IP injection of exendin-4/TDM, showed a rapid and immediate decrease in blood glucose levels.

Also exendin-4 administered about 15-30 minutes ahead of the glucose bolus (before time 0 in FIG. 3; data not shown) produced an even more pronounced lowering of blood glucose effect, because the absorption of the hormone takes a certain amount of time to be absorbed and to be active. Thus, exendin-4 (or Exenatide) which is currently in human clinical trials, when combined with alkyl glycosides of the invention, effectively treats a hyperglycemic condition by lowering the blood glucose levels of the hyperglycemic subject.

EXAMPLE 8

Alkyglycosides have Antibacterial Activity by Reducing Bacterial Log Growth

The cultures of *Candida albicans* (ATCC No. 10231), *Aspergillus niger* (ATCC No. 16404), *Escherichia coli*

(ATCC No, 8739), *Pseudomonas aeruginosa* (ATCC No. 9027), and *Staphylococcus aureus* (ATCC No. 6538) were obtained from American Type Culture Collection, 10801 University Boulevard, Manassas, Va. 20110-2209. The viable microorganisms used in the invention were not more than five passages removed from the original ATCC culture. As described herein, one passage is defined as the transfer of organisms from an established culture to fresh medium and all transfers are counted.

by turbidimetric measurements for the challenge microorganisms. The suspension should be refrigerated if it is not used within 2 hours. To confirm the initial cfu per mL estimate, the number of cfu per mL in each suspension was determined using the conditions of media and microbial recovery incubation times listed in Table IV (e.g., from about 3 to about 7 days). This value serves to calibrate the size of inoculum used in the test. The bacterial and yeast suspensions were used within 24 hours of harvest; whereas the fungal preparation can be stored under refrigeration for up to 7 days.

TABLE IV

Culture Conditions for Inoculum Preparation

| Organism | Suitable Medium | Incubation Temperature | Inoculum Incubation Time | Microbial Recovery Incubation Time |
|---|---|---|---|---|
| *Escherichia coli* (ATCC No. 8739) | Soybean-Casein Digest Broth; Soybean-Casein Digest Agar | 32.5 ± 2.5 | 18 to 24 hours | 3 to 5 days |
| *Staphylococcus aureus* (ATCC No. 6538) | Soybean-Casein Digest Broth; Soybean-Casein Digest Agar | 32.5 ± 2.5 | 18 to 24 hours | 3 to 5 days |
| *Candida albicans* (ATCC No. 10231) | Sabouraud Dextrose Agar; Sabouraud Dextrose Broth | 22.5 ± 2.5 | 44 to 52 hours | 3 to 5 days |
| *Aspergillus niger* (ATCC No. 16404) | Sabouraud Dextrose Agar; Sabouraud Dextrose Broth | 22.5 ± 2.5 | 6 to 10 days | 3 to 7 days |

Cultures received from the ATCC are resuscitated according to the directions provided by the ATTC. Cells grown in broth were pelleted by centrifugation, resuspended in $\frac{1}{20}$th the volume of fresh maintenance broth, and combined with an equal volume of 20% (v/v in water) sterile glycerol. Cells grown on agar were scraped from the surface into the maintenance broth also containing 10% glycerol broth. Small aliquots of the suspension were dispensed into sterile vials and the vials were stored in liquid nitrogen or in a mechanical freezer at a temperature no higher than about −50° C. When a fresh seed-stock vial was required, it was removed and used to inoculate a series of working stock cultures. These working stock cultures were then used periodically (each day in the case of bacteria and yeast) to start the inoculum culture.

All media described herein should be tested for growth promotion using the microorganisms indicated above under Test Organisms.

To determine whether the alkyl saccharides of the invention inhibit growth or have antibacterial activity, the surface of a suitable volume of solid agar medium was inoculated from a fresh revived stock culture of each of the specified microorganisms. The culture conditions for the inoculum culture is substantially as described in Table IV. For example, suitable media can include but is not limited to, Soybean-Casein Digest or Sabouraud Dextrose Agar Medium. The bacterial and *C. albicans* cultures was harvested using sterile saline TS, by washing the surface growth, collecting it in a suitable vessel, and adding sufficient sterile saline TS to obtain a microbial count of about $1 \times 10^8$ colony-forming units (cfu) per mL. To harvest the cells of *A. niger*, a sterile saline TS containing 0.05% of polysorbate 80 was used, and then adding sufficient sterile saline TS to obtain a count of about $1 \times 10^8$ cfu per mL.

Alternatively, the stock culture organisms may be grown in any suitable liquid medium (e.g., Soybean-Casein Digest Broth or Sabouraud Dextrose Broth) and the cells harvested by centrifugation, and washed and resuspended in sterile saline TS to obtain a microbial count of about $1 \times 10^8$ cfu per mL. The estimate of inoculum concentration was determined To determine which alkylglycoside formulations have antibacterial activity, the formulations were prepared in phosphate buffered saline (PBS) at pH 7. As a source of nutrition, either 1.5 mg/mL bovine serum albumin (BSA; see Tables V and VI) or 1 mg/mL of PYY was added (see Table VII) to the medium. BSA (CAS Number: 9048-46-8) was obtained from Sigma-Aldrich, St. Louis, Mo., USA, n-dodecyl-4-O-α-D-glucopyranosyl-β-D-glucopyranoside and n-tetradecyl-4-O-α-D-glucopyranosyl-β-D-glucopyranoside were obtained from Anatrace Inc., Maumee, Ohio, USA, and PYY was obtained from Bachem California Inc., Torrance, Calif., USA.

Antibacterial activity of the alkylglycosides were conducted in four sterile, capped bacteriological containers of suitable size into which a sufficient volume of alkylglycoside solution had been transferred. Each container was inoculated with one of the prepared and standardized inoculums and mixed. The volume of the suspension inoculum was between about 0.5% and about 1.0% of the volume of the alkylglycoside solution. The concentrations of test microorganisms added to the alkylglycoside solution was such that the final concentrations of the test preparation after inoculation was between about $1 \times 10^5$ and $1 \times 10^6$ cfu per mL of alkylglycoside solution. To determine the level of inhibition of growth, or reduction of growth based on a logarithmic scale, the initial concentration of viable microorganisms in each test preparation was estimated based on the concentration of microorganisms in each of the standardized inoculum as determined by the plate-count method. The inoculated containers were then incubated at about 22.5° C.±2.5. The growth or non-growth of the microorganisms in each culture/container were again determined at day 14 and day 28. The number of cfu present in each calculation was determined by the plate-count procedure standard in the art for the applicable intervals. The change in the orders of magnitude of bacterium and/or fungi was then determined by subtracting the first calculated log 10 values of the concentrations of cfu per mL present at the start or beginning (e.g., day 0), from the log 10 values of the concentration of cfu per mL for each microorganism at the applicable test intervals (e.g., day 14 and day 28; see Tables V, VI and VII).

TABLE V

Log reduction of microorganisms in cultures containing 0.125% n-Dodecyl-4-O-α-D-glucopyranosyl-β-D-glucopyranoside

| Staphlococcus aureus | Escherichia Coli | Candida albicans | Aspergillus niger |
|---|---|---|---|
| Day 0 | | | |
| 7.3 × 10$^5$ (cfu/gm) | 1.2 × 10$^5$ (cfu/gm) | 3.2 × 10$^5$ (cfu/gm) | 4.8 × 10$^5$ (cfu/gm) |
| Day 14 | | | |
| ≥5.2 orders of magnitude reduction | N.D. | 3.0 orders of magnitude reduction | 0.7 orders of magnitude reduction |
| Day 28 | | | |
| ≥5.2 orders of magnitude reduction | 0.1 orders of magnitude reduction | ≥5.3 orders of magnitude reduction | No growth from initial count |

TABLE VI

Log Reductions in cultures containing 0.2% n-Tetradecyl-4-O-α-D-glucopyranosyl-β-D-glucopyranoside

| Staphlococcus aureus | Escherichia Coli | Candida albicans | Aspergillus niger |
|---|---|---|---|
| Day 0 | | | |
| 7.3 × 10$^5$ (cfu/gm) | 1.2 × 10$^5$ (cfu/gm) | 3.2 × 10$^3$ (cfu/gm) | 4.8 × 10$^5$ (cfu/gm) |
| Day 14 | | | |
| ≥5 orders of magnitude reduction | N.D. | 3.0 orders of magnitude reduction | 0.5 orders of magnitude reduction |
| Day 28 | | | |
| ≥5 orders of magnitude reduction | No growth from initial count | ≥5.4 orders of magnitude reduction | No growth from initial count |

TABLE VII

Log reduction of cultures containing 0.25% n-Dodecyl-4-O-α-D-glucopyranosyl-β-D-glucopyranoside

| Staphlococcus aureus | Escherichia Coli | Candida albicans | Aspergillus niger |
|---|---|---|---|
| Day 0 | | | |
| 7.3 × 10$^5$ (cfu/gm) | 1.2 × 10$^5$ (cfu/gm) | 3.2 × 10$^5$ (cfu/gm) | 4.8 × 10$^5$ (cfu/gm) |
| Day 14 | | | |
| ≥4.9 orders of magnitude reduction | ≥5 orders of magnitude reduction. | ≥4.5 orders of magnitude reduction. | 4.7 orders of magnitude reduction |
| Day 28 | | | |
| ≥4.9 orders of magnitude reduction | ≥5 orders of magnitude reduction. | ≥4.5 orders of magnitude reduction. | 4.7 orders of magnitude reduction |

Determining the antibacterial activity of other alkylglycosides would occur substantially as described herein.

EXAMPLE 9

Administration of Alkyglycosides with Antisense Oligonucleotides to Primates

An approximately 7,000 Dalton antisense oligonucleotide (ASO) with a modified backbone (phosphorothioate oligonucleotide as described in U.S. Pat. No. 7,132,530) mixed with alkylglycoside tetradecyl-beta-D-maltoside (Intravail™), was administered to six Cynomolgus monkeys canulated into the jejunum at a dose of 10 mg/kg. The animals were fasted prior to administration. Test agents were dissolved in PBS buffer and injected through the cannula into the jejunum of each animal in a 1.5 mL volume or administered subcutaneously (s.c.) as noted in Table VIII.

TABLE VIII

Bioavailability of Antisense Drugs Administered With Tetradecyl-Beta-D-Maltoside

| Test Agents | Average Bioavailability (n = 6) | Observations |
|---|---|---|
| ASO (no tetradecyl-beta-D-maltoside) intrajejunal | 0% (undetectable) | Intestinal villi completely intact |
| ASO administered s.c. at 0.5 mg/kg. | 100% | Intestinal villi completely intact |
| 10 mg ASO + 50 mg/kg tetradecyl-beta-D-maltoside A5 intrajejunal | 18% +/− 7% | Intestinal villi completely intact |
| 10 mg ASO + 50 mg/kg sodium caprate intrajejunal | 9% +/− 7% | The tops of some of the intestinal villi were found to be missing |

The protocol involved a 3 way crossover in which each animal had the first 3 test agents in Table VIII administered on 3 different dates. There was a 1 week washout period between dosing dates. Two of the animals were subsequently given a fourth test agent containing 5% sodium caprate as an absorption enhancer. Analysis of the blood levels was conducted using quantitative analysis involving solid phase extraction using cationic polystyrene nanoparticles.

Solid-phase extractions of the blood samples were first performed. Nanoparticle-oligonucleotide conjugates were formed using a known amount of oligonucleotide added to an aliquot of each sample (200-400 μl) and diluted with 800 μl of 50 mM Tris.HCl (pH 9) in deionized water. The mixture was briefly vortexed prior to the addition of 200 μl of a polystyrene nanoparticle suspension prepared by surfactant-free emulsion polymerization using water-soluble cationic initiators to induce a positive surface charge (solid content: approximately 10 mg/ml). The mixture was subsequently vortexed again. After 5-10 min of incubation, the suspension was centrifuged and the supernatant removed. The particles were resuspended in 1 ml of a solution of 0.5 M acetic acid in deionized water/ethanol (1:1) and separated from the washing solution by centrifugation. After the supernatant was removed, the particles were resuspended in 1 ml of deionized water and separated by another centrifugation step. 200 μl of a solution of 150 μM SDS in aqueous ammonia (25%)/acetonitrile ($^{60}/_{40}$) was added to the nanoparticle-oligonucleotide conjugates and the released oligonucleotides were separated from the carrier by centrifugation. In order to exclude contamination of the samples with residual particles, the supernatant was placed in another 1.5-ml tube and centrifuged again. Subsequently, the samples were dried by rotoevaporation or lyophilization and stored at −20° C. until analysis.

Quantitative analysis was performed with capillary gel electrophoresis of the extracted samples. Capillary gel electrophoresis (CGE) was performed with a capillary electrophoresis system. An oligonucleotide analysis kit containing polyvinyl alcohol (PVA) coated capillaries, polymer solution B, and oligonucleotide buffer was obtained. Using PVA-coated capillaries, analysis was carried out using the manufactures protocol.

Using the data obtained from CGE analysis, quantitation of phosphorothioate oligonucleotides was carried out. The amount of oligonucleotides in the samples ($n_{ON}$) was calculated using the following formula:

$$n_{ON} = n_{Std}(\epsilon_{Std}/\epsilon_{ON})((A_{ON}/T_{ON})/(A_{Std}/T_{Std})),$$

where $n_{Std}$ is the amount of standard oligonucleotide added to the sample, $\epsilon_{Std}$ and $\epsilon_{ON}$ are the molar extinction coefficients, and $A_{Std}/T_{Std}$ and $A_{ON}/T_{ON}$ are the corrected peak areas (quotient of peak area and migration time) of the standard and the investigated compound, respectively. The quotient of the corrected peak areas of the analyte and the standard is referred to as the normalized area.

AUC's were calculated from the concentration vs. time cures over a 240 minute period. The relative bioavailabilities were determined as the ratio of each AUC divided by the AUC for the intravenously administered drug. Intravail™ (tetradecyl-beta-D-maltoside) excipient provided bioavailability up to 18%. The control showed no detectable absorption without a surfactant excipient. The sodium caprate formulation showed an average bioavailability of 9%.

Throughout this application, various publications are referenced. The disclosures of these publications in their entireties are hereby incorporated by reference into this application in order to more fully describe the state of the art to which this invention pertains.

Birkett et al., (1991) "Bioavailability and first pass clearance," *Austra Prescr* 14:14-16.

Birkett et al., (1990) "How drugs are cleared by the liver," *Austra Prescr* 3:88-89.

Hovgaard et al., (1996) "Stabilization of insulin by alkylmaltosides: A spectroscopic evaluation," *Int. J. Pharmaceutics* 132:107-113.

Hovgaard et al., (1996) "Stabilization of insulin by alkylmaltosides. B. Oral absorption in vivo in rats," *Int. J. Pharmaceutics* 132:115-121.

Tetsuaki et al. (1997) "Lysis of *Bacillus subtilis* cells by glycerol and sucrose esters of fatty acids," *Applied and Environmental Microbiology,* 53(3):505-508.

Watanabe et al., (2000) "Antibacterial carbohydrate monoesters suppressing cell growth of *Streptococcus mutan* in the presence of sucrose," *Curr Microbiol* 41(3): 210-213.

Although the present process has been described with reference to specific details of certain embodiments thereof in the above examples, it will be understood that modifications and variations are encompassed within the spirit and scope of the invention. Accordingly, the invention is limited only by the following claims.

What is claimed is:

1. A method of increasing the bioavailability of an oligonucleotide in a subject by administering a composition comprising the oligonucleotide and an absorption increasing amount of an alkylglycoside to the subject via an oral, rectal or gastrointestinal delivery route, wherein the alkylglycoside comprises a maltose linked by glycosidic linkage to an alkyl chain comprising between 10 to 16 carbons, thereby increasing the bioavailability of the oligonucleotide in the subject.

2. The method of claim 1, wherein the oligonucleotide is an RNA interference molecule.

3. The method of claim 1, wherein the oligonucleotide is an antisense oligonucleotide.

4. The method of claim 1, wherein the oligonucleotide contains one or more phosphorothioate linkages.

5. The method of claim 1, wherein the alkylglycoside is selected from the group consisting of dodecyl maltoside, tridecyl maltoside, and tetradecyl maltoside.

6. The method of claim 1, wherein the alkylglycoside is tetradecyl-beta-D-maltoside.

7. The method of claim 1, wherein the oligonucleotide has a molecular weight from about 5-10 kD.

8. The method of claim 1, wherein the alkylglycoside is dodecyl-beta-D-maltoside.

9. The method of claim 1, wherein the composition further comprises citric acid, sodium citrate, propylene glycol, glycerin, ascorbic acid, sodium metabisulfite, ethylenediaminetetraacetic acid (EDTA), benzalkonium chloride, sodium hydroxide, or combinations thereof.

10. The method of claim 9, wherein the composition further comprises ethylenediaminetetraacetic acid (EDTA).

11. The method of claim 1, wherein the composition is administered via the oral delivery route.

12. The method of claim 1, wherein the composition is administered via the rectal delivery route.

13. The method of claim 1, wherein the composition is administered via the gastrointestinal delivery route.

14. The method of claim 1, wherein the alkylglycoside is present in the composition at a concentration of 0.01% to 20% by weight.

15. The method of claim 1, wherein the oligonucleotide comprises a modified sugar moiety, a modified base moiety, a modified sugar linking moiety, or combination thereof.

16. The method of claim 1, wherein the oligonucleotide comprises a modified linkage selected from the group consisting of phosphoramide, phosphorothioate, phosphorodithioate, methyl phosphonate, phosphotriester, phosphoramidate, O-methylphosphoroamidite, peptide, and combinations thereof.

* * * * *